(12) United States Patent
Adachi et al.

(10) Patent No.: US 9,332,357 B2
(45) Date of Patent: *May 3, 2016

(54) UNCOMFORTABLE SOUND PRESSURE ESTIMATION SYSTEM, UNCOMFORTABLE SOUND PRESSURE ESTIMATION APPARATUS, UNCOMFORTABLE SOUND PRESSURE ESTIMATION METHOD, AND COMPUTER PROGRAM THEREOF

(71) Applicant: Panasonic Corporation, Osaka (JP)

(72) Inventors: Shinobu Adachi, Nara (JP); Jun Ozawa, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 244 days.

This patent is subject to a terminal disclaimer.

(21) Appl. No.: 14/081,392

(22) Filed: Nov. 15, 2013

(65) Prior Publication Data
US 2014/0072130 A1 Mar. 13, 2014

Related U.S. Application Data

(63) Continuation of application No. PCT/JP2013/001515, filed on Mar. 8, 2013.

(30) Foreign Application Priority Data

Mar. 19, 2012 (JP) .................................. 2012-061453

(51) Int. Cl.
*H04R 25/00* (2006.01)
*A61B 5/0484* (2006.01)
*A61B 5/12* (2006.01)

(52) U.S. Cl.
CPC ............ *H04R 25/30* (2013.01); *A61B 5/04845* (2013.01); *A61B 5/125* (2013.01); *H04R 25/70* (2013.01)

(58) Field of Classification Search
CPC ........ H04R 25/70; H04R 25/30; H04R 25/50; H04R 2225/41

USPC .................................................... 381/60, 314
See application file for complete search history.

(56) References Cited

U.S. PATENT DOCUMENTS

| | | | | |
|---|---|---|---|---|
| 5,139,028 A | * | 8/1992 | Steinhaus | A61B 5/0006 600/508 |
| 5,630,425 A | * | 5/1997 | Panescu | A61B 5/0422 128/901 |

(Continued)

FOREIGN PATENT DOCUMENTS

| JP | 2004-179965 A | 6/2004 |
|---|---|---|
| JP | 2004-337294 A | 12/2004 |

(Continued)

OTHER PUBLICATIONS

International Search Report for International Application No. PCT/JP2013/001515 mailed Apr. 2, 2013.

(Continued)

*Primary Examiner* — Alexander Jamal
(74) *Attorney, Agent, or Firm* — Renner, Otto, Boisselle & Sklar, LLP

(57) ABSTRACT

An exemplary uncomfortable sound pressure estimation system includes: a sound stimulation scheduling section configured to determine points in time of outputting a group of sound stimulations so that times of measurement for event-related potentials in response to the second sound and third sound arrive after a predetermined noise-lingering time has elapsed since a next point of occurrence of periodic noise; an event-related potential characteristic amount extraction section configured to receive the points in time of outputting the sound stimulation group, and extract a characteristic amount of an event-related potential of the electroencephalogram signal based on each point of outputting the group of sound stimulations as a starting point; and an uncomfortable sound pressure determination section configured to determine an uncomfortable sound pressure for the frequency of the sound stimulation group.

13 Claims, 15 Drawing Sheets

(56) References Cited

U.S. PATENT DOCUMENTS

| | | | | |
|---|---|---|---|---|
| 6,115,628 | A | * | 9/2000 | Stadler .............. A61B 5/0452 600/517 |
| 8,543,195 | B1 | * | 9/2013 | Brockway ........... A61B 5/0402 600/300 |
| 2009/0259277 | A1 | * | 10/2009 | Cornejo Cruz .... A61B 5/04845 607/57 |
| 2012/0029383 | A1 | * | 2/2012 | Henriksen ............. A61B 5/12 600/559 |

FOREIGN PATENT DOCUMENTS

| | | |
|---|---|---|
| JP | 2009-195571 A | 9/2009 |
| JP | 2009-288354 A | 12/2009 |
| WO | WO 2008/038650 | 4/2008 |

OTHER PUBLICATIONS

Thornton et al., "The objective estimation of loudness discomfort level using auditory brainstem evoked responses", Scand Audiol. 1987; 16(4): 219-25.

Zenker-Castro et al., "Auditory Steady-State Responses and Hearing Device Fitting", In G. Rance (Ed.), Plural Publishing (2008), pp. 241-263.

"Jishoukanrendeni (ERP) Manyuaru -P300 Wo Chushinni—(or "Event-Related Potential (ERP) Manual -mainly concerning P300-")", edited by Kimitaka Kaga et al., Shinohara Shuppan Shinsha, (1995), p. 30.

Pascoe, D.P. "Clinical measurements of the auditory dynamic range and their relation to formulas for hearing aid gain", In Iensen. H. I. (Ed.) Hearing Aid Fitting: Theoretical and Practical Views 13th Danavox Symposium. Copenhagen: Stougaard. (1988), pp. 129-152.

* cited by examiner

*FIG.1*

|  | RIGHT | | | LEFT | | |
|---|---|---|---|---|---|---|
|  | 1000 | 2000 | 4000 | 1000 | 2000 | 4000 |
| 1 | 90 | 97.5 | 90 | 90 | 90 | 85 |
| 2 | 92.5 | 87.5 | 90 | 92.5 | 87.5 | 90 |
| 3 | 107.5 | 105 | 105 | 110 | 110 | 110 |
| 4 | 110 | 110 | 105 | 105 | 102.5 | 102.5 |
| 5 | 110 | 110 | 110 | 110 | 110 | 110 |
| 6 | 92.5 | 95 | 95 | 85 | 80 | 82.5 |
| 7 | 107.5 | 107.5 | 102.5 | 105 | 102.5 | 102.5 |
| 8 | 107.5 | 110 | 100 | 97.5 | 102.5 | 110 |
| 9 | 100 | 100 | 95 | 95 | 92.5 | 90 |
| 10 | 107.5 | 110 | 110 | 105 | 105 | 105 |
| 11 | 95 | 95 | 90 | 102.5 | 97.5 | 95 |
| 12 | 97.5 | 95 | 90 | 90 | 90 | 85 |
| 13 | 110 | 107.5 | 110 | 105 | 97.5 | 107.5 |
| 14 | 97.5 | 97.5 | 95 | 92.5 | 87.5 | 85 |
| 15 | 90 | 87.5 | 87.5 | 85 | 82.5 | 82.5 |
| 16 | 92.5 | 92.5 | 92.5 | 90 | 90 | 90 |
| 17 | 102.5 | 107.5 | 102.5 | 100 | 105 | 107.5 |
| 18 | 92.5 | 92.5 | 82.5 | 92.5 | 90 | 87.5 |
| AVERAGE | 100.1 | 100.4 | 97.4 | 97.4 | 95.7 | 96.0 |
| STANDARD DEVIATION | 7.4 | 7.8 | 8.3 | 7.9 | 8.9 | 10.3 |

UPPER VIEW        FRONTAL VIEW

*FIG.13*

UNCOMFORTABLE SOUND PRESSURE (dBHL)

|  | 1000 Hz | 2000 Hz | 4000 Hz |
|---|---|---|---|
| RIGHT | 105 | 100 | 100 |
| LEFT | 100 | 95 | 100 |

*FIG. 16*

| HTL VALUE dBHL | ESTIMATED UCL VALUE dBHL |
|---|---|
| 0 | 97 |
| 5 | 99 |
| 10 | 99 |
| 15 | 98 |
| 20 | 97 |
| 25 | 101 |
| 30 | 102 |
| 35 | 101 |
| 40 | 103 |
| 45 | 105 |
| 50 | 107 |
| 55 | 108 |
| 60 | 110 |
| 65 | 114 |
| 70 | 115 |
| 75 | 117 |
| 80 | 120 |
| 85 | 120 |
| 90 | 124 |
| 95 | 130 |
| 100 | 127 |

UNCOMFORTABLE SOUND PRESSURE ESTIMATION SYSTEM, UNCOMFORTABLE SOUND PRESSURE ESTIMATION APPARATUS, UNCOMFORTABLE SOUND PRESSURE ESTIMATION METHOD, AND COMPUTER PROGRAM THEREOF

This is a continuation of International Application No. PCT/JP2013/001515 with an international filing date of Mar. 8, 2013, which claims priority of Japanese Patent Application No. 2012-061453, filed on Mar. 19, 2012, the contents of which are hereby incorporated by reference.

BACKGROUND

1. Technical Field

The present disclosure relates to a technique of estimating an uncomfortable sound pressure by using electroencephalogram.

2. Description of the Related Art

Hypacusia means difficulty in hearing sounds of a specific frequency or a frequency band, for example. The frequency or frequency band which presents hearing difficulty differs from user to user.

A hearing aid amplifies sounds so that the user can hear the sounds. The necessary amount of amplification differs for each user because auditory characteristics are different from user to user.

Prior to beginning use of a hearing aid, fitting is conducted to determine a gain for each sound frequency. In order to perform fitting, it is necessary to accurately measure the auditory characteristics of a user.

In an auditory characteristics test, a hearing threshold level (HTL) is determined first. Next, an uncomfortable level (UCL) is determined. The HTL and the UCL are used for determining a dynamic range of sound pressure for sounds to be output from a hearing aid.

Methods of measuring UCL by using electroencephalogram are being developed.

For example, the document of Thornton, A. R., Yardley, L., & Farrell, G. (1987), "The objective estimation of loudness discomfort level using auditory brainstem evoked responses. Scandinavian Audiology, 16, 219-225" (referred to as "Document 1" hereinafter) discloses that there is correlation between a V wave latency of an auditory brainstem response (ABR) to a click sound and the UCL.

The document of Zenker-Castro, F., & Barajas de Prat, J. J. (2008), Auditory steady-state responses and hearing device fitting Part A: The role of auditory steady-state responses in fitting hearing aids. (pp. 241-258). In G. Rance (Ed.), The auditory steady-state response: Generation, recording, and clinical application. San Diego: Plural, (referred to as "Document 2" hereinafter) discloses that, from the amplitude of an auditory steady state response (ASSR) to an amplitude-modulation sound, the loudness felt by the person can be approximated. With the technique described in Document 2, frequency-by-frequency UCL estimation is impossible, and the estimation requires 30 minutes or more, and the accuracy of estimation may be low for loud sounds that are near the UCL.

SUMMARY

In the aforementioned conventional technique, while preventing a user from being uncomfortable as much as possible, it is desired to determine the UCL of the user with a good precision. Moreover, in the case where periodic noises may possibly affect the electroencephalogram, it is desired to determine the UCL with a good precision.

One non-limiting, and exemplary embodiment of the present disclosure provides a technique that allows an uncomfortable sound pressure of a user to be estimated with an improved precision, without presenting any overbearing sound to the user. Another non-limiting, and exemplary embodiment of the present disclosure provides a technique that allows a UCL of a user to be estimated with a good precision in an environment where periodic noises may possibly affect electroencephalogram measurement.

In one general aspect, an uncomfortable sound pressure estimation system disclosed herein comprises: a biological signal measurement section configured to measure an electroencephalogram signal of a user; an output section configured to present a sound stimulation to the user; a characteristic amount extraction section configured to extract a characteristic amount of an event-related potential associated with the sound stimulation, from the electroencephalogram signal in a predetermined analysis zone defined based on a point in time of presenting the sound stimulation as a starting point; an uncomfortable sound pressure determination section configured to determine an uncomfortable sound pressure for a frequency of the sound stimulation group, based on the characteristic amount extracted by the characteristic amount extraction section; a periodic noise extraction section configured to, from the electroencephalogram signal of the user, extract a point of occurrence of at least one of a plurality of noises constituting periodic noises; a noise occurrence prediction section configured to predict a next point of noise occurrence from the point of occurrence of the at least one noise extracted by the periodic noise extraction section; and a sound stimulation scheduling section configured to determine an output timing for the sound stimulation, based on the next point of noise occurrence predicted by the noise occurrence prediction section.

According to the above aspect, it is possible to estimate with a good precision the UCL of a user who is wearing a device that may generate periodic noises, without causing the user to hear any overbearing sound.

The general or specific embodiment above can be implemented by using a system, an apparatus, a method, or a computer program, or implemented by using a combination of a system, an apparatus, a method, and/or a computer program.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF DRAWINGS

FIG. 1 is a diagram showing examples of subjectively reported values of uncomfortable sound pressure in a subjective report experiment conducted by the inventors.

FIG. 13 is a diagram showing an example of result accumulation in a result accumulating DB.

FIG. 16 is a diagram showing exemplary estimated UCL values for different HTL values.

DETAILED DESCRIPTION

Figure 2:
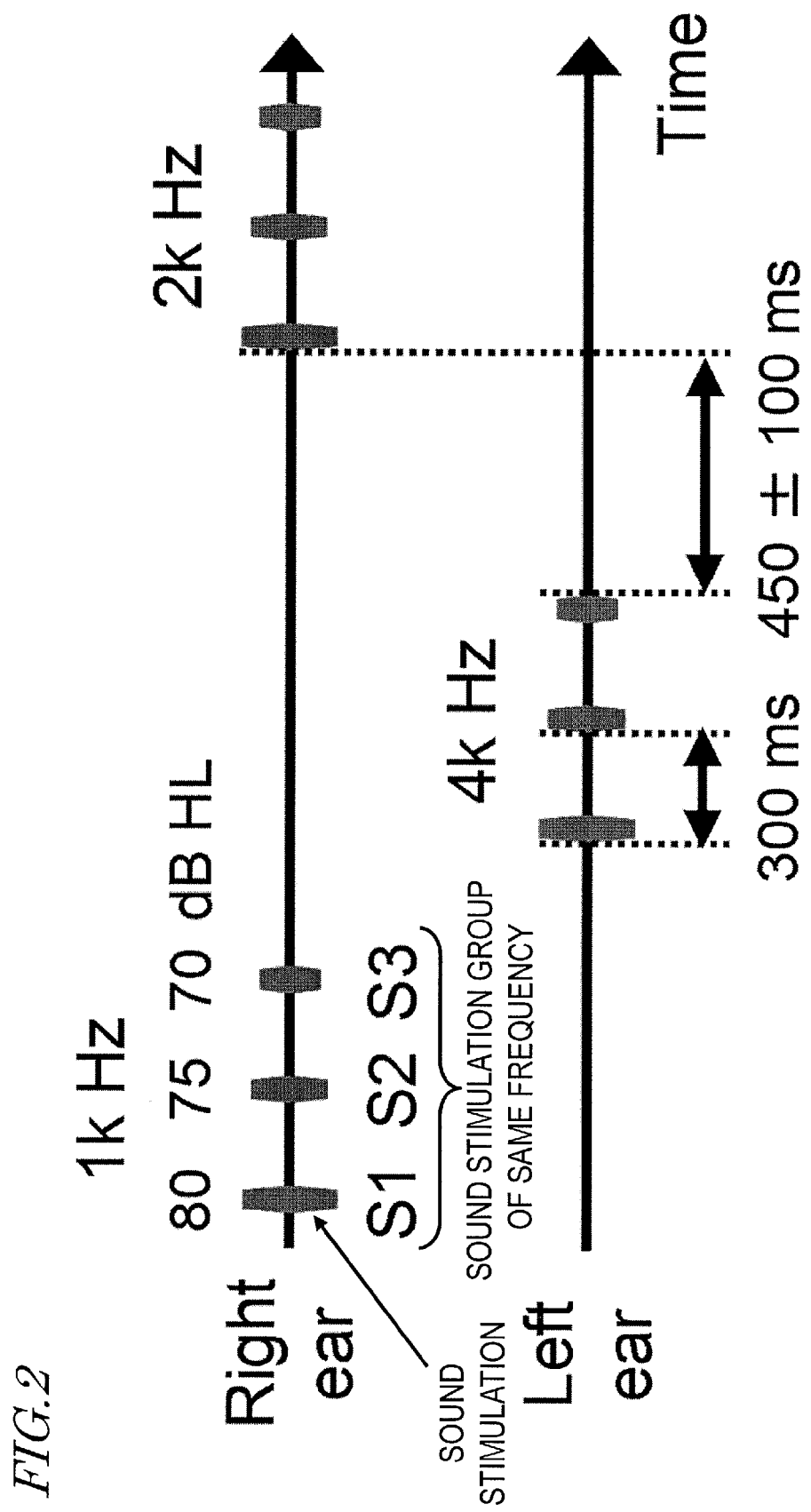
FIG. 2 is a diagram showing exemplary sound stimulations used in an electroencephalographic experiment conducted by the inventors.

The conventional techniques described in Document 1 and Document 2 above adopt a method which, after a user is placed in an uncomfortable state by presenting a sound stimulation with sound pressure of an uncomfortable level to the user, determines whether the sound pressure of that sound stimulation is the UCL or not. In other words, an approach of examining an uncomfortable sound pressure based on whether the user is in an uncomfortable state or not is adopted. Therefore, in order to conduct a hearing evaluation, an overbearing sound must be presented to the user, and the user actually needs to be thus placed in an uncomfortable state.

On the other hand, according to one embodiment of the uncomfortable sound pressure estimation system in the present disclosure, while preventing a user from being uncomfortable as much as possible, his or her UCL is determined with a good precision. Hereinafter, with reference to the attached drawings, embodiments of the uncomfortable sound pressure estimation system according to the present disclosure will be described.

First, the definitions of the terms used in the present specification will be described.

An "event-related potential (ERP)" is a fluctuation in the potential of an electroencephalogram (EEG) that occurs in response to a stimulation.

A "sound stimulation", also referred to as an auditory stimulation, is a sound which is presented to a user.

An "N1 component" is a negative component of event-related potential which appears at about 100 ms since the point of presenting a sound stimulation as a starting point.

A "P2 component" is a positive component of event-related potential which appears at about 200 ms since the point of presenting a sound stimulation as a starting point.

"Latency" is the time, based on the point of presenting an audio stimulation as a starting point, until a peak potential of a positive component or a negative component appears.

A "negative component" generally refers to a potential which is smaller than 0 μV. In a comparison between two potentials, the potential having the greater negative value may be referred to as a negative component between the two.

A "positive component" generally refers to a potential which is greater than 0 μV. In a comparison between two potentials, the potential having the greater value may be referred to as a positive component between the two.

An "uncomfortable sound pressure (uncomfortable loudness level: UCL)" is a sound pressure which is so loud that it is felt uncomfortable to a user.

A "hearing threshold level (HTL)" is the sound pressure of a softest sound that is audible to a user, which may simply be referred to as a threshold value.

"Presenting a sound" means outputting a pure tone.

A "pure tone" is a tone which repetitively undergoes periodic oscillation, such that it is expressed as a sine wave having only one frequency component.

In the present specification, in order to define a component of an event-related potential, a point in time after the lapse of a predetermined time since a given point is expressed by referring to a "latency of about 100 ms", for example. This means possible inclusion of a range around the specific point of 100 ms. Generally speaking, there are 30 to 50 ms of differences (shifts) in event-related potential waveform between individuals, according to table 1 on p. 30 of "JISHOUKANRENDENI (ERP) MANYUARU—P300 WO CHUSHINNI—(or "Event-Related Potential (ERP) Manual—mainly concerning P300—"), edited by Kimitaka KAGA et al., Shinohara Shuppan Shinsha, 1995)". Therefore, the terms "about X ms" and "near X ms" mean that a breadth of 30 to 50 ms may exist before or after X ms (e.g., 100 ms±30 ms, 200 ms±50 ms).

According to the present disclosure, a sound stimulation of a sound pressure that does not constitute an uncomfortable sound pressure for the user is presented; an induced electroencephalographic response to the presented sound is measured; and based on a result of analyzing the induced electroencephalographic response, a UCL of that user is estimated. As a result, without allowing the user to hear an overbearing sound that would be felt uncomfortable, the UCL of that user can be estimated.

According to the present disclosure, a sound stimulation of a sound pressure that is not felt uncomfortable to the user is presented to the user; an induced electroencephalographic response to the presented sound is measured; and based on a result of analyzing the induced electroencephalographic response, a UCL of the user is estimated. As a result, without allowing the user to hear an overbearing sound that is felt uncomfortable, the UCL of the user can be estimated.

Hereinafter, with reference to the attached drawings, embodiments of the uncomfortable sound pressure estimation system according to the present disclosure will be described.

In an uncomfortable sound pressure estimation system of the below-described embodiment, a sound stimulation with sound pressure of a level that is not felt uncomfortable to the user is presented at appropriate timing, so as to avoid noises that periodically mix in the electroencephalogram (called "periodic noises"), and thus an uncomfortable sound pressure is estimated with a high precision.

Prior to describing the estimation system, method, etc. of uncomfortable sound pressure, experiments which have been conducted and the experimental results there of will be described. Then will be described a method of controlling the timing of sound stimulation presentation in order to estimate an uncomfortable sound pressure with a high precision even in a situation where there is noise periodically mixing in the electroencephalogram.

(Description of Experimental Outline)

1. Experimental Outline

The inventors have conducted the following two experiments, with a view to realizing an uncomfortable sound pressure estimation based on electroencephalogram.

One is a subjective report experiment of measuring a UCL based on subjective reporting. The subjective report experiment was conducted before and after an electroencephalogram measurement experiment (see below). The UCL data obtained from this subjective report experiment was used as reference data against which a UCL is to be estimated from the electroencephalogram described below.

Another is an electroencephalogram measurement experiment of measuring responses to sound stimulations. In the electroencephalogram measurement experiment, pure tones of the same frequency were presented totaling three times in succession, with monotonously-descending sound pressure changes of every 5 dB, and event-related potentials in response to the respective sound stimulations of first to third sounds were measured.

Hereinafter, sound stimulations being presented a plurality of times successively with monotonously-descending sound pressure changes may also be referred to as "decrescendo stimulations". Event-related potentials to such sound stimulations were acquired for use as data in UCL value estimation.

As a result, the inventors have found that a UCL conforming to subjective reporting can be estimated even when decrescendo stimulations are presented at sound pressures lower than a sound pressure which is generally evaluated to be the UCL, by applying linear discrimination to a change pattern of wavelet coefficients calculated through wavelet transform of event-related potentials in response to the first to third sounds.

Herein, it is assumed that a sound pressure lower than a sound pressure which is generally evaluated to be the UCL varies depending on the HTL value. For example, according to works of Pascoe (Pascoe, D. P. (1988). (Clinical measurements of the auditory dynamic range and their relation to formulas for hearing aid gain. In Jensen. H. 1. (Ed.) Hearing Aid Fitting: Theoretical and Practical Views 13th Danavox Symposium. Copenhagen: Stougaard.)), a value which is at least 5 dB lower than an estimated UCL value for each HTL value as shown in FIG. 16 may be designated the aforementioned "sound pressure lower than a sound pressure which is generally evaluated to be the UCL".

Note that it is when a sound stimulation has a sound pressure which is higher than the HTL that any event-related potential will be induced in response to that sound stimulation. In other words, a range of sound pressures lower than a sound pressure which is generally evaluated to be the UCL should be a range of sound pressures higher than the HTL. With this technique, a UCL estimation is achieved in a short time and with a high accuracy, without presenting overbearing sounds.

Hereinafter, the experiments conducted by the inventors and the results thereof, and characteristic features of electroencephalogram which have been found through their analysis will be described in detail.

(Description of Experimental Conditions)

2. UCL Subjective Report Experiment and Electroencephalogram Measurement Experiment Through these experiments, a UCL which is measured through subjective reporting will be compared against a UCL which is estimated from an auditory evoked potential (AEP) in response to a sound stimulation, thus discussing the feasibility of UCL estimation based on AEP.

Hereinafter, a UCL which is measured through subjective reporting may be denoted as "subjective UCL", whereas a UCL which is estimated from AEP may be denoted as an "estimated UCL".

Informed consent was obtained from 18 male adults with normal hearing, who were no longer in school (25 to 56 years old, with an average of 39.6±8.4 years old), who agreed to participate in the experiments.

2-1. UCL Subjective Report Experiment

By using an audiometer (AA-72, manufactured by RION), discontinuous sounds at 1 kHz, 2 kHz, 4 kHz were presented to one ear at a time, by an ascending method. A hand was raised any time it was felt so loud that it could not be heard for a long time, and this was recorded as a subjective UCL for each of the right or left ear and each frequency. The subjective UCL measurement was conducted one time each before and after the electroencephalogram measurement.

Hereinafter, results of the subjective report experiment will be described. All participants were people with normal hearing. However, the results of the subjective report experiment greatly differed from individual to individual. For example, for the same frequency, there was a difference in subjective UCL of 40 dB between individuals at the most.

This indicates that the definition of "unbearably loud" may greatly from individual to individual. Thus, it can be said that UCL measurement through subjective reporting is difficult.

FIG. 1 shows UCL measurement results of individuals which were measured through subjective reporting in the subjective report experiment. FIG. 1 indicates average values of two measurement results each. The sound pressure is in units of dBHL. As can be seen from the standard deviation for the right or left ear and for each different frequency shown in FIG. 1, there are some fluctuations in the subjective UCL value. It can be seen that there are relatively large fluctuations in subjective UCL value among individuals.

2-2. Electroencephalogram Measurement Experiment

In the electroencephalographic experiment, for each of three frequencies (1000 Hz (1 kHz), 2000 Hz (2 kHz), 4000 Hz (4 kHz)), sound stimulations were presented at three sound pressures (80, 75, 70 dBHL) lower than a sound pressure which is generally evaluated to be the UCL. The three sound pressures were monotonously descending. Then, a characteristic change in the event-related potential for each sound stimulation was examined.

In the present specification, "monotonously descending" means that each next sound has a smaller sound pressure than the previous sound.

Hereinafter, with reference to FIG. 2, FIG. 3A, FIG. 3B, and FIG. 4, the experimental setting and experimental results of the electroencephalogram measurement experiment will be described.

FIG. 2 shows sound stimulations that were presented to the right ear and the left ear. In FIG. 2, the horizontal axis represents time.

As each sound stimulation, a tone burst sound with a rise and fall of 3 ms and a duration of 44 ms was used.

Three sound stimulations of the same frequency were presented to each of the right ear and left ear, with a sound pressure decrement of every 5 dB from 80 dBHL. The sound stimulations had an interval of 300 ms. Moreover, by setting the frequency of the sound stimulations at each of 1 kHz, 2 kHz, and 4 kHz, and the experiment was conducted for frequency. Thus, for a set consisting of three sound stimulations of the same frequency, the experiment was conducted under six conditions, i.e., three frequencies by two ears for presentation.

In the present specification, the aforementioned three sound stimulations will be referred to as the first sound, second sound, and third sound in the order of presentation (i.e., in descending order of sound pressure herein), respectively denoted as S1, S2, and S3. Moreover, a plurality of sound stimulations of the same frequency may be referred to as a "sound stimulation group".

The interval from the end time of the third sound (S3) that is contained in a preceding sound stimulation group till the start time of the first sound (S1) contained in a current sound stimulation group was 450±50 ms.

In order to reduce the influence of accustomization of a person on the electroencephalogram, it was ensured that successive sounds of the same frequency would not be presented. For each of the six conditions, 50 successive sounds were presented, totaling 300 times. Each participant was instructed to silently listen to the sound to be heard. No response in action was asked for.

The sound stimulations were output from a PC via headphones (HDA200, manufactured by SENNHEISER). The sound pressure of each sound stimulation was subjected to calibration by using a noise level meter (LA-1440, manufactured by ONO SOKKI) and a coupler (IEC318, manufactured by Larson Davis).

Figure 3A:
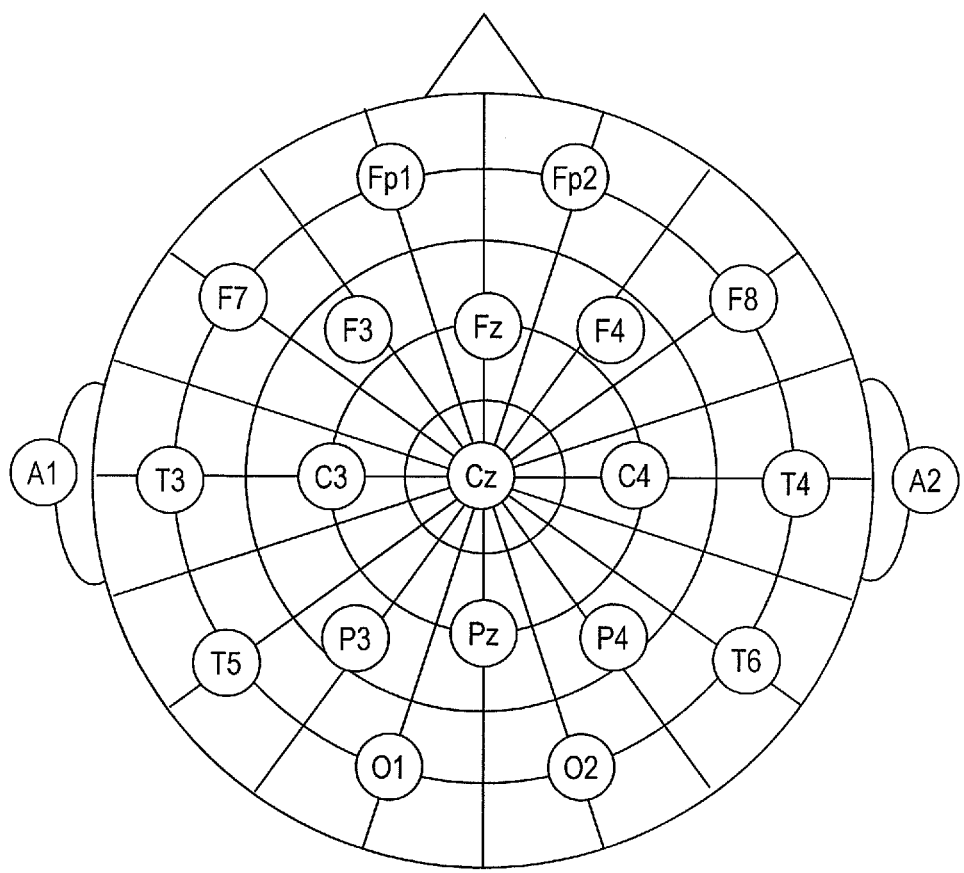
FIGS. 3A and 3B are diagrams each showing electrode positions according to the International 10-20 system, and electrode positions in an electroencephalographic experiment conducted by the inventors.
Figure 3B:
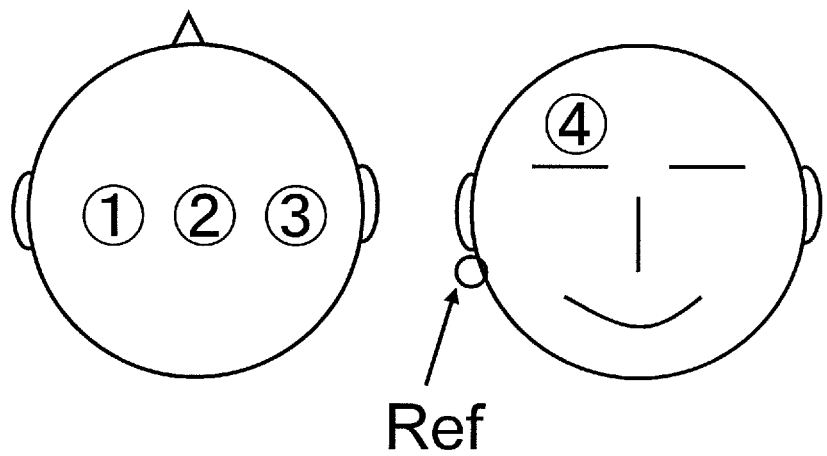

Next, the positions of electrodes to be worn for electroencephalogram measurement will be described. FIG. 3A shows electrode positions according to the International 10-20 system (10-20 System). FIG. 3B shows the positions of electrodes worn in this experiment. In FIG. 3B, circled numbers 1, 2, and 3 represent electrode positions C3, Cz, and C4, respectively.

The inventors measured as the electroencephalogram potential differences between active electrodes worn at C3, Cz, and C4 (the International 10-20 system) on the scalp and an active electrode worn above the right eye (circled number in FIG. 3B) and a reference electrode worn at the right mastoid. A "mastoid" is a protrusion of the cranium below the hind root of an ear. FIG. 3B shows the mastoid position as "Ref".

The sampling frequency was 1000 Hz; the time constant was 1 second. A 1-20 Hz band-pass filter was applied off-line. From S1 as a starting point, a waveform from −100 ms to 1000 ms (400 ms after presenting S3) was cut out, which was subjected to an arithmetic mean for each of the right or left ear and each frequency, whereby an AEP was obtained. As used herein, "−100 ms" means a point in time which is 100 milliseconds before the point in time at which S1 is presented. Those trials which exhibited a potential exceeding ±80 μV at any electrode were excluded from the arithmetic mean, because they presumably are under the influence of noises, e.g., eye movements and blinks.

On the other hand, in order to extract a time-frequency component contained in the electroencephalogram, the electroencephalogram having been downsampled to 100 Hz was subjected to a wavelet transform. A coefficient (wavelet coefficient) that is obtained through the wavelet transform corresponds to time-frequency information of the electroencephalogram.

As a mother wavelet, the Mexican hat ($\phi(t)=(1t^2)\exp(t^2/2)$) was used. The wavelet coefficient was scaled on integers from 1 to 9 (corresponding to 2.5-12.5 Hz).

Then, for each ear (right or left ear) for presentation and each sound stimulation frequency, an arithmetic mean of wavelet coefficients was taken to determine an evoked potential (AEP) for each of the successive sounds. The following was excluded from the analysis: data of a person whose subjective UCL was not correctly measured due to being out of the scale; and data of three people for whom the number of summations was less than 15 in the AEP calculation for each of the right or left ear and each frequency.

A UCL estimation was made by applying a discriminant analysis (linear discrimination) to the evoked potentials (wavelet characteristic amounts) thus obtained in response to the successive sounds.

Specifically, by dividing the range from 0 ms to 900 ms of an arithmetic-meaned wavelet coefficient into 50 ms time windows, a wavelet characteristic amount was generated by taking an average of wavelet coefficients for each scale (unit of division). Moreover, arbitrary two wavelet characteristic amounts were combined, and the correspondence in pairs of subjective UCLs and wavelet characteristic amounts of participants other than the participant in question was learned for use as training data. The training data was generated for each sound stimulation frequency, by using electroencephalograms which were measured by presenting sound stimulations to the right or left ear.

The precision of UCL estimation was evaluated based on an average error (i.e., an average of absolute values of differences between the subjective UCL and the estimated UCL for each of the right or left ear and each frequency of every participant analyzed). The average error was determined for every combination of wavelet characteristic amounts (totaling 13041 combinations).

3. Experimental Results

Hereinafter, results of the electroencephalogram measurement experiment will be described.

First, in order to confirm that an index of uncomfortable sound pressure estimation exists in the event-related potential against changing sound pressure, arithmetic-meaned event-related potentials were compared against the subjective UCL value. If participant-to-participant differences in subjective UCL value are reflected by differences in event-related potential, then it should be possible to estimate an uncomfortable sound pressure from an event-related potential.

Now, as discussed above, the subjective UCL value can only be an index that is prone to fluctuations among participants, because of different personalities existing with respect to overbearing sounds. Therefore, in order to reduce such fluctuations, event-related potentials were arithmetic-meaned and compared while making a distinction between the two groups of large subjective UCL values and small subjective UCL values. Specifically, an arithmetic mean was taken with respect to the cases for the subjective UCL value for each participant and for each frequency was 100 dBHL or more, or the cases where it was less than 100 dBHL. Note that 100 dBHL is a value near the center of the subjective UCL values of all participants obtained from the subjective report experiment.

Figure 4:
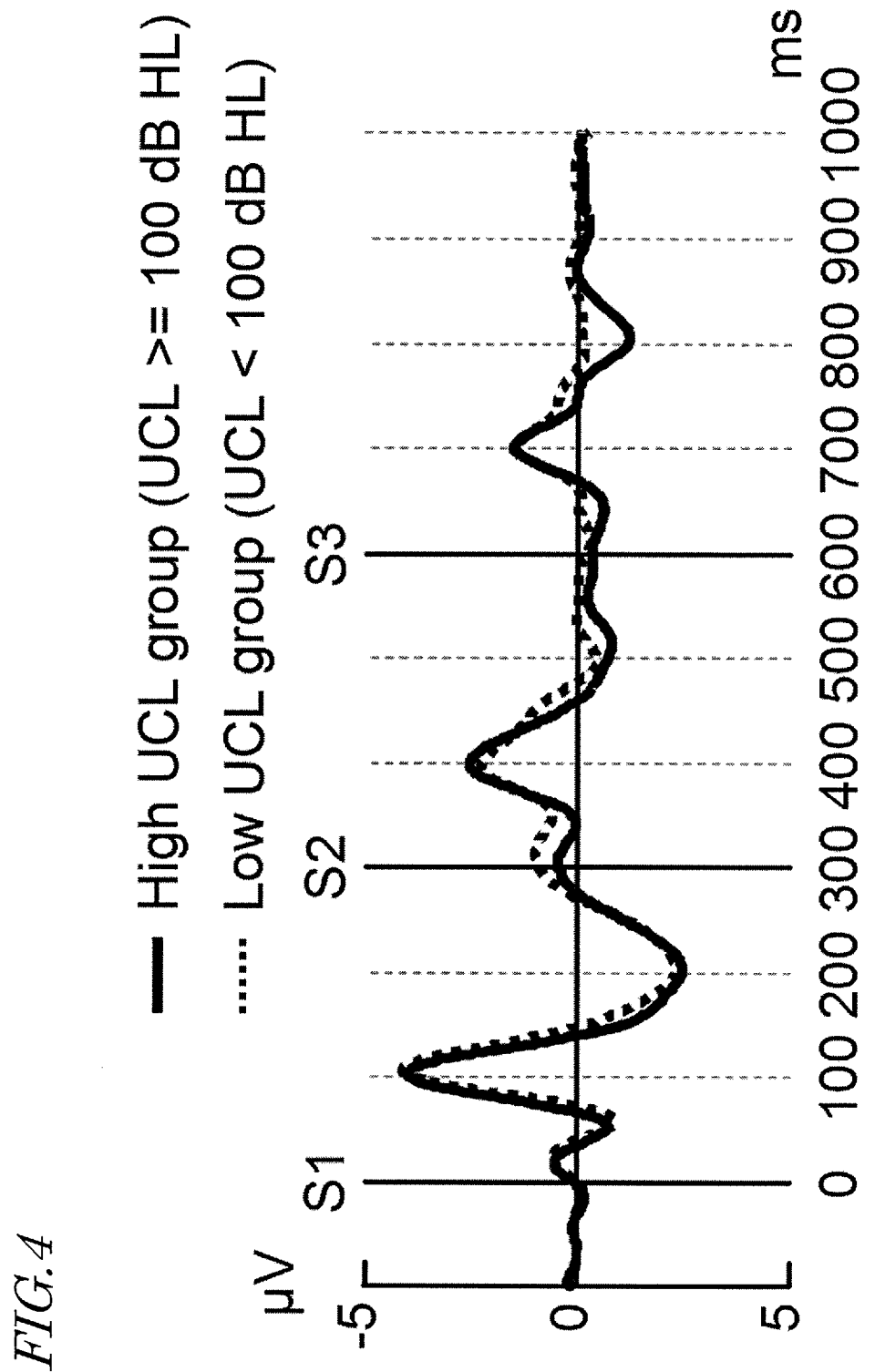
FIG. 4 is a diagram showing exemplary characteristic data of event-related potential in an electroencephalographic experiment conducted by the inventors.

FIG. 4 shows total arithmetic mean waveforms of event-related potential each corresponding to a potential difference between the electrode at the central portion (Cz) and the reference electrode. Each waveform shown in FIG. 4 is a waveform obtained by adding up measured event-related potentials for each condition and taking an average thereof.

Hereinafter, a waveform obtained through such addition and averaging will be referred to as a total arithmetic mean waveform.

In FIG. 4, the bold line represents a total arithmetic mean waveform of participants having a subjective UCL of 100 dBHL or more (high UCL group), whereas the broken line represents a total arithmetic mean waveform of participants having a subjective UCL lower than 100 dBHL (low UCL group).

Vertical solid lines indicate the timing of presenting S1, S2, and S3 (0 ms, 300 ms, 600 ms).

Irrespective of whether the subjective UCL is high or low, a negative component (N1 component) appears at about 100 ms since each sound stimulation is presented, and a positive component (P2 component) appears at about 200 ms since each sound stimulation is presented.

Moreover, the difference in waveform between the high UCL group and the low UCL group is greater in the waveforms in response to S2 and S3 than in the waveform in response to S1. It can be seen that, in the waveforms in response to S2 and S3, the high UCL group has a smaller amplitude than the low UCL group. This indicates that event-related potential (in particular, event-related potentials associated with S2 and S3) may serve as an index of UCL estimation.

Next, a UCL estimation based on the wavelet coefficients obtained in the above-described manner will be described.

Figure 5:
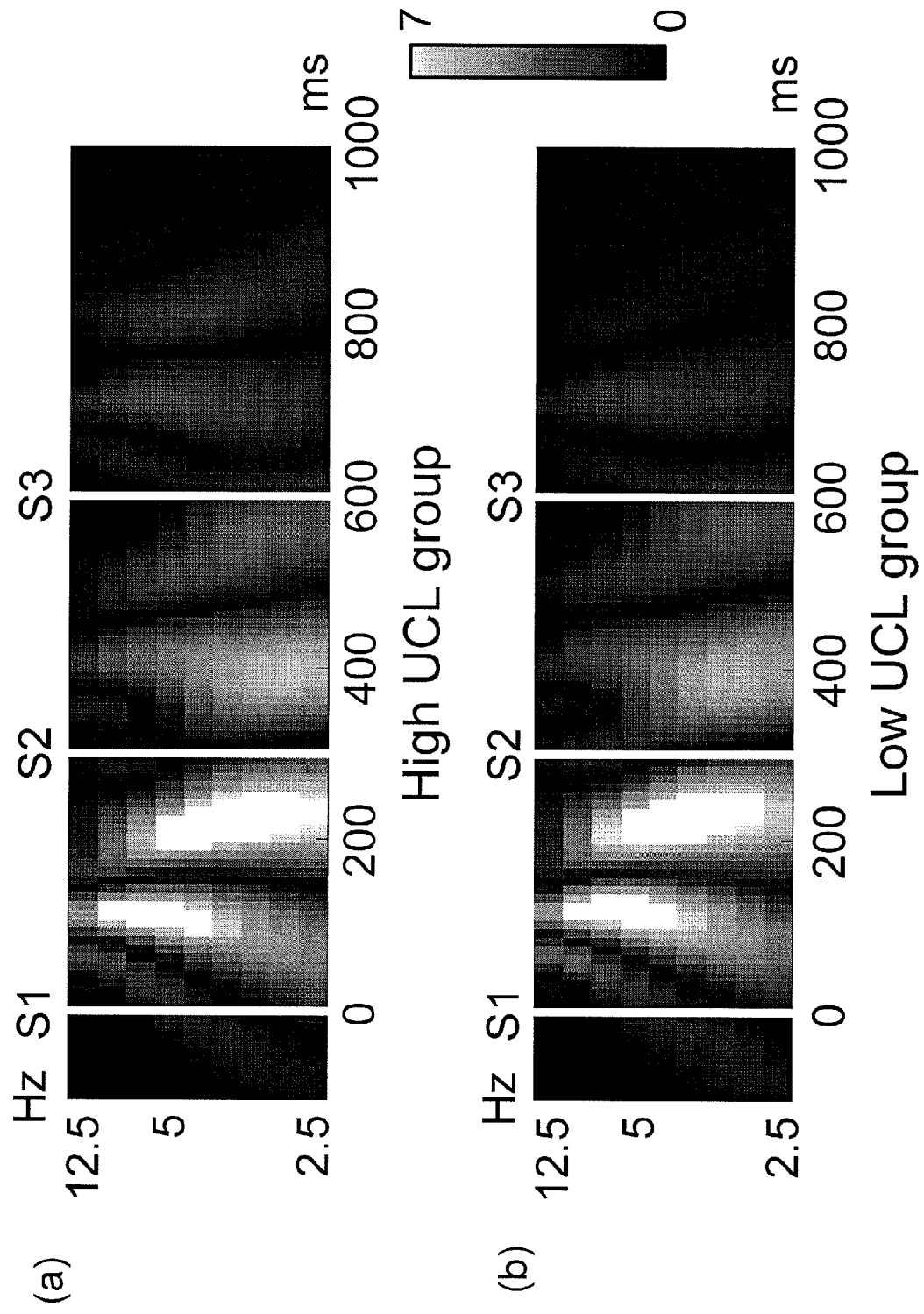
FIG. 5 is a diagram showing exemplary wavelet coefficients of event-related potentials in an electroencephalographic experiment conducted by the inventors.

Portions (a) and (b) of FIG. 5 show total arithmetic mean wavelet coefficients of the high UCL group and the low UCL group. In portions (a) and (b) of FIG. 5, intensity (i.e., size of the wavelet characteristic amount) is shown by gradation, where greater intensities are indicated by darker portions and smaller intensities are indicated by lighter portions. It can be seen that, in the waveform with respect to S3, for example, the low UCL group has smaller responses than the high UCL group at 5 Hz or less.

Figure 6:
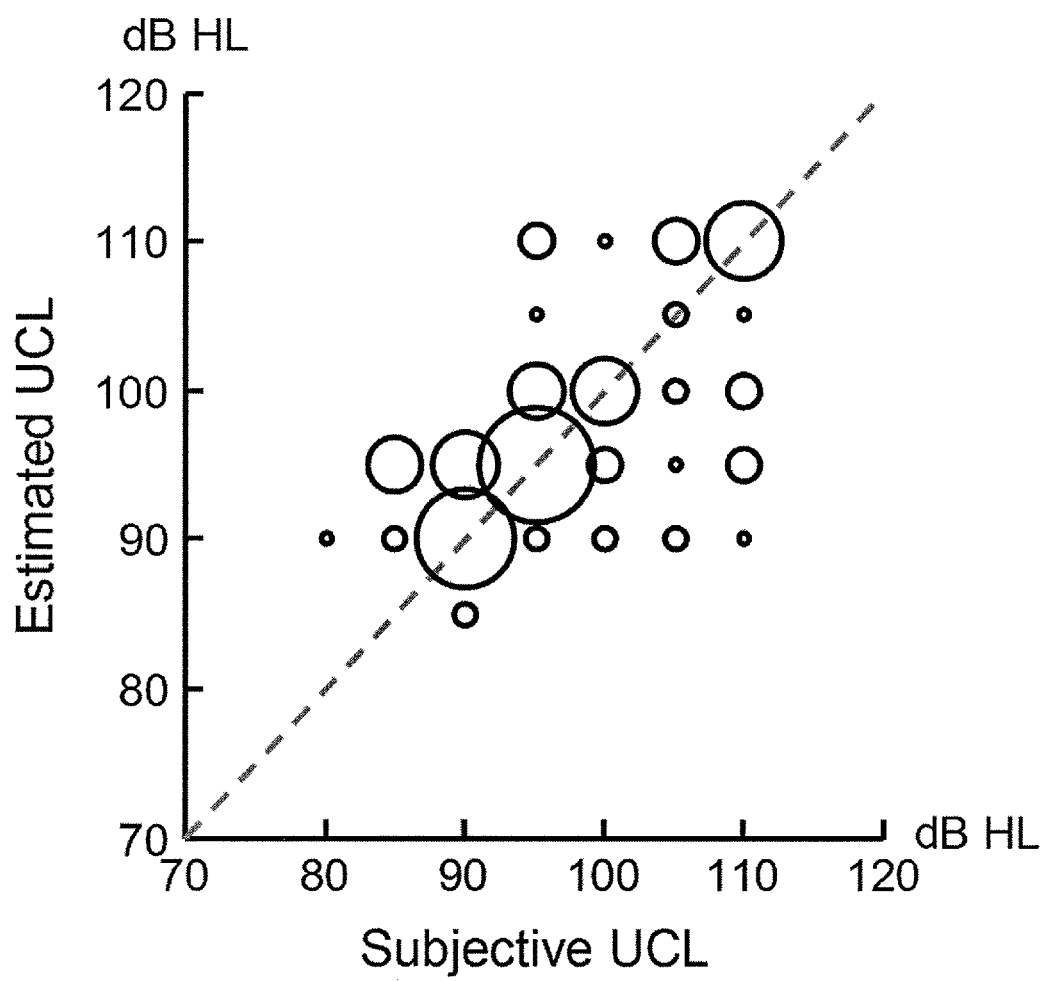
FIG. 6 is a diagram showing fluctuations in subjectively reported values obtained from a subjective report experiment and results of uncomfortable sound pressure estimation from an electroencephalographic experiment.

FIG. 6 shows a distribution of UCLs estimated by using the time-frequency information of electroencephalogram in the above-described linear discrimination and subjective UCLs. The results are given regardless of the right or left ear and the stimulation frequency. At each lattice point, frequency is indicated by a circle symbol in a corresponding size.

FIG. 6 also shows a broken line which defines the cases of equal subjective UCL and estimated UCL. In other words, any circle symbol whose center is on the broken line indicates a case where the estimated UCL matches the subjective UCL.

Despite some fluctuations between the estimated UCLs and the subjective UCLs, it can be seen that UCL estimation is being achieved by using the time-frequency information of electroencephalogram. There was an average error of 4.9±5.0 dB. In 72.6% of all, the estimation error was 5 dB or less, and the coefficient of correlation between actual measurements and estimated values was r=0.566.

Figure 7:
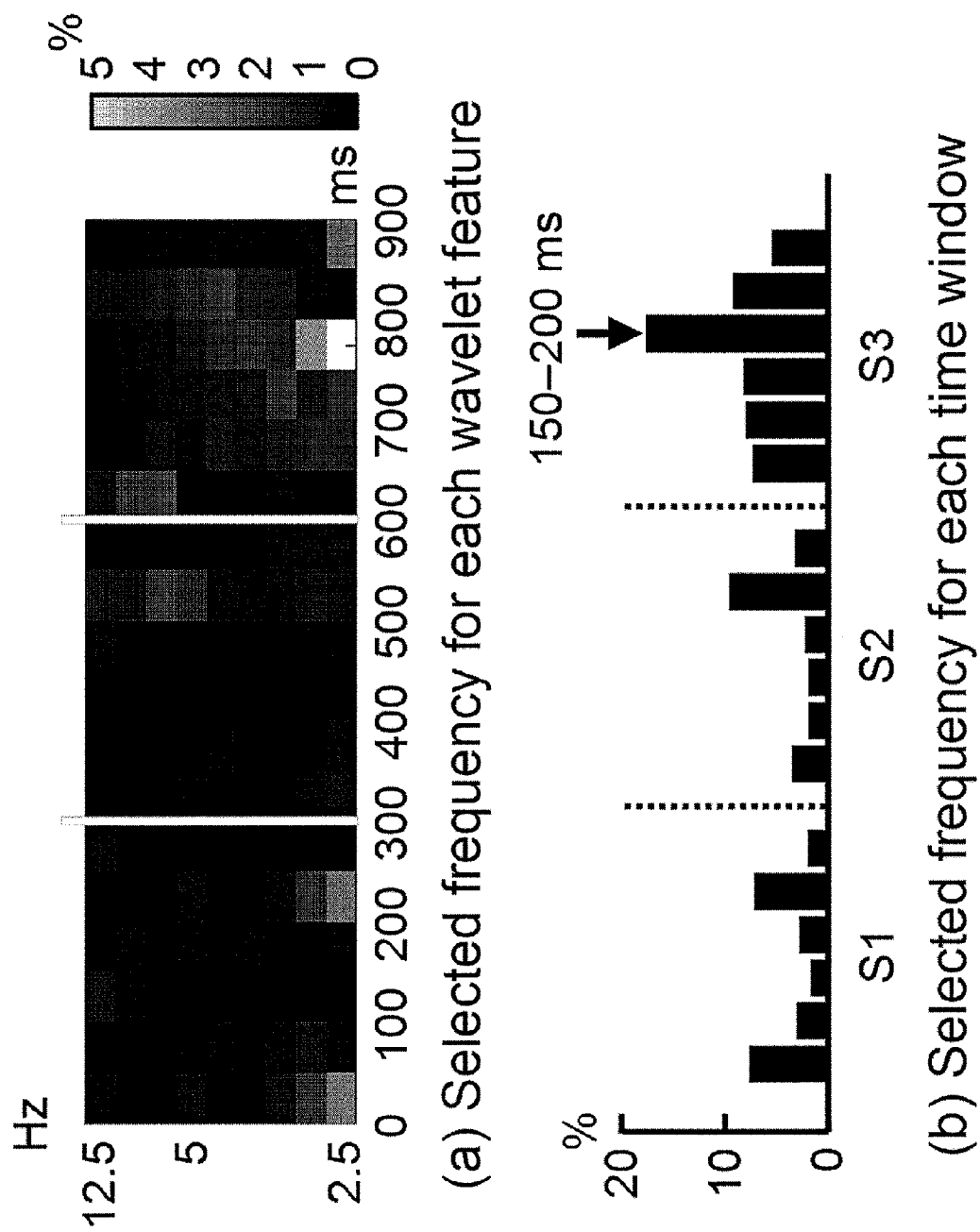
FIG. 7 is a diagram showing occurrence frequencies of wavelet characteristic amounts used in the upper 1% estimations exhibiting least average errors between subjectively reported values and electroencephalographically estimated values.

A portion (a) of FIG. 7 shows occurrence frequencies of wavelet characteristic amounts used in the upper 1% estimations exhibiting least average errors. A portion (b) of FIG. 7 shows, in different time windows, occurrence frequencies of wavelet characteristic amounts used in the upper 1% estimations.

It can be seen from portions (a) and (b) of FIG. 7 that the wavelet characteristic amount after S3 presentation is valid for UCL estimation. In particular, wavelet characteristic amounts at 150-200 ms since S3 presentation are used with an occurrence frequency of 15% or more, among the upper 1% estimations. This zone coincides with the zone with large differences in total arithmetic mean waveform shown in FIG. 4.

Thus, the inventors have arrived at the following two findings through the experiments.

The first is that, as can be seen from FIG. 4, the difference in event-related potential waveform between the high UCL group and the low UCL group is greater in the waveforms with respect to S2 and S3 than the waveform with respect to S1.

The second is that, as can be seen from FIG. 5 and FIG. 7, the time-frequency information of electroencephalogram at S3 is valid for UCL estimation.

In other words, it became clear that the event-related potentials in response to S2 and S3 differ depending on whether the subjective UCL is high or low, the amplitude being smaller in the case of low subjective UCLs.

Moreover, as a result of applying linear discrimination to the wavelet characteristic amounts, UCL estimation was achieved with an average error of 5 dB or less.

The average error was particularly small when estimation was made by using the wavelet characteristic amounts in response to S3 (in particular at 150-200 ms since S3 presentation). These results suggest that the event-related potential after S3 presentation contains UCL information, and that analysis thereof would enable UCL estimation.

An average error between the measured subjective UCLs and the estimated UCLs was 4.9±5.0 dB. Considering that generic audiometers are graduated in 5 dB and that there was 4.0±4.3 dB of fluctuation between two measured subjective UCLs, this error would be tolerable in auditory characteristics measurement.

Relative to S1, the event-related potentials in response to S2 and S3 decayed in amplitude. This is a result of successively presenting sound stimulations at short intervals. From the experiments by the inventors, it became clear that the decay characteristics differ depending on whether the subjective UCL is high or low, such that greater decays occur in the low UCL group than in the high UCL group. A possible interpretation of this phenomenon may be that tolerance for loud sounds is related to the duration of refractory periods. It may be inferred that encephalic processing of S1 did not complete in time in the low UCL group, thus preventing analysis of S2 and S3 (i.e., AEP was suppressed).

On the other hand, the AEP in response to S1 did not show much difference irrespective of high or low UCL, and was not used as frequently as S3 in the upper 1% estimations. The N1 component amplitude in response to sound stimulations in a sound pressure range that will daily come to the ear undergoes an essentially linear increase in accordance with the sound pressure levels of the sound stimulations. This indicates a possibility that an AEP in response to S1 reflects the physical characteristics of the sound stimulation but contains hardly any UCL information. Therefore, in order to realize a UCL estimation that imposes little burden on the user by using sound stimulations of sound pressures which are daily experienced by the ear, it should be effective to successively present a plurality of sound stimulations.

It is considered that a similar tendency will result also by conducting a discriminant analysis with not only wavelet characteristic amounts but also the information of P1-N1 amplitude and N1-P2 amplitude. Note that an N1-P2 amplitude represents the absolute value of a difference between the negative amplitude of an N1 component and the positive amplitude of a P2 component. A P1-N1 amplitude is similarly defined.

An event-related potential containing a P1 component, an N1 component, or a P2 component is defined in terms of the time from sound stimulation presentation until peak generation (latency), the amplitude level of that component, and the like, and therefore is considered dependent on the time-frequency relationship.

Moreover, when the aforementioned discriminant analysis is to be conducted, the training data may be generated irrespective of the right or left ear and frequency.

(Method of Controlling the Timing of Stimulation Presentation when Periodic Noises are Mixed)

Figure 8:
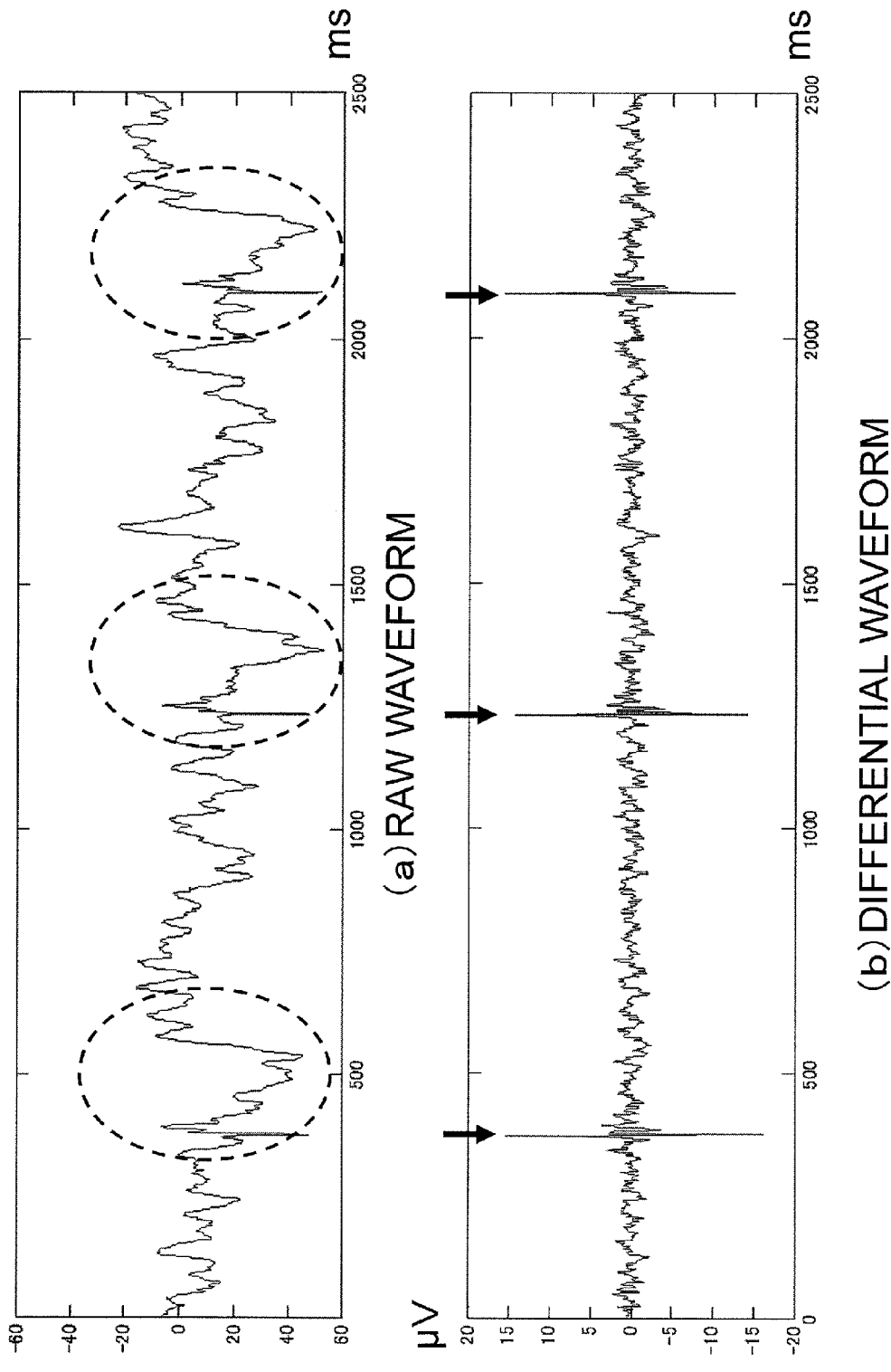
FIG. 8 is a diagram showing an example of periodic noises recorded by the inventors.

An electroencephalogram measured of a user who is wearing a pacemaker will exhibit noises occurring with the timing of pulsation. A portion (a) of FIG. 8 shows a result obtained by the inventors recording an electroencephalogram of a person wearing a pacemaker. The electroencephalogram was recorded under similar settings to the above.

A portion (a) of FIG. 8 shows a portion of the raw waveform corresponding to the potential difference between a reference electrode attached at the right mastoid and a reference electrode attached at the central portion (Cz). In a portion (a) of FIG. 8, the vertical axis represents potential ($\mu$V), and the horizontal axis represents time (ms).

In the raw waveform level, it can be seen that large noises with an amplitude of about 50 $\mu$V are mixed due to pulsation, each noise lasting for about 250 ms since the beginning of the occurrence. Without being limited to a pacemaker, it is considered that similar noises on the electroencephalogram will also be induced by periodic noises generated from any other electrical device (e.g., an electrostimulator for rehabilitation purposes or an artificial valve).

A portion (b) of FIG. 8 shows a waveform obtained by subjecting the raw waveform of a portion (a) of FIG. 8 to first-order differentiation. It can be seen that the starting points of noises associated with pulsation are clearly detectable through differentiation (arrows in a portion (b) of FIG. 8).

These are substantial noises that deteriorate the precision of uncomfortable sound pressure estimation. As is shown in FIG. 4, waveform differences of 5 $\mu$V or less are utilized for effective UCL estimations. Therefore, noises of several dozen $\mu$V, even if not in temporal synchronization with the stimulations, will presumably increase the estimation error.

One method of reducing the influence of such periodic noises may be setting a stringent criterion for determining ignorable trials when obtaining an event-related potential. However, if trials having a potential exceeding $\pm 30$ $\mu$V are ignored, for example, there will be a problem in that most trials are not eligible for addition because of periodic noises, thus resulting in a prolonged test time. Another method is disclosed in Japanese Laid-Open Patent Publication No. 2009-195571, in which a template waveform of periodic noises is generated and subtracted from the raw waveform. However, in the case where an electroencephalogram is to be measured via a dry electrode without using paste, the contact resistance between the scalp and the electrode will fluctuate over time, so that the noise component associated with pulsation will also fluctuate in amplitude; thus, a simple subtraction of the template waveform will not remove the noises.

Therefore, the inventors have studied a method of controlling the timing of presenting sound stimulations to alleviate deterioration in the precision of uncomfortable sound pressure estimation. Thus, the inventors have found that, by presenting sound stimulations with appropriate timing at which periodic noises are unlikely to affect the uncomfortable sound pressure estimation, uncomfortable sound pressure estimation can be achieved with a high precision. Note that the present technique can also be used in conjunction with the aforementioned conventional method which involves subtraction of a template waveform.

Figure 9:
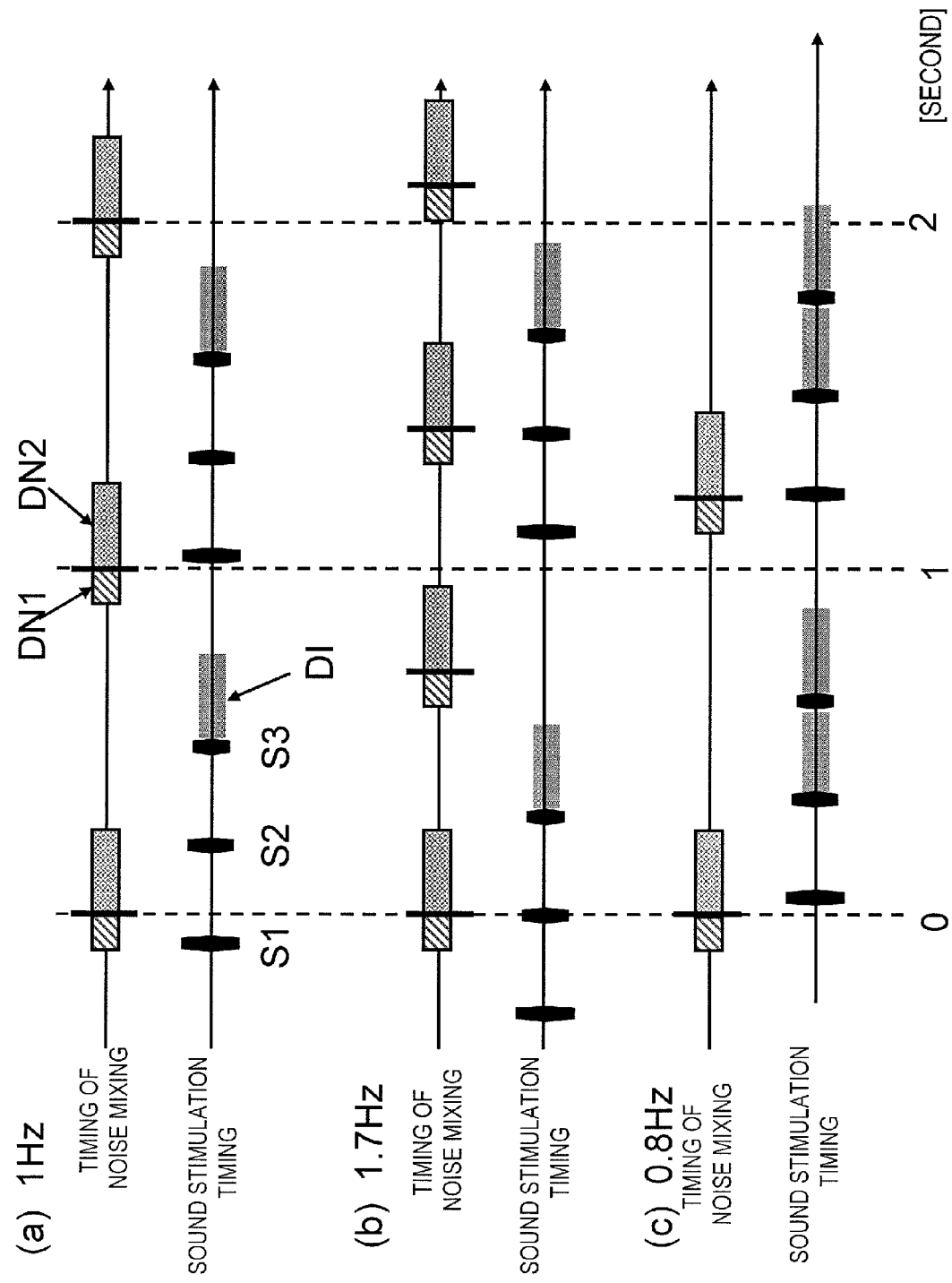
FIG. 9 is a diagram showing examples of timing of stimulation presentation conceived by the inventors, in which periodic noises exert reduced influence on the accuracy of estimation.

Portions (a) to (c) of FIG. 9 show a temporal relationship between periodic noises and sound stimulation timing according to an embodiment of the present disclosure. A portion (a) of FIG. 9 shows a case where periodic noises are mixed at 1 Hz (heart rate: 60); a portion (b) of FIG. 9 shows a case where periodic noises are mixed at 1.7 Hz (heart rate about 100); and a portion (c) of FIG. 9 shows a case where periodic noises are mixed at 0.8 Hz (heart rate: 48).

The inventors have found a method which measures event-related potentials in response to the aforementioned second sound and third sound, while reducing noise influences by controlling the points of occurrence (timing) of sound stimulations based on the points in time at which noise occurs and the duration for which an electroencephalogram is affected by a noise after occurrence of that noise. This will be specifically described below.

Hereinafter, a point in time at which a noise occurs may also be denoted as "a point of noise occurrence", and the duration for which an electroencephalogram is affected by a noise after occurrence of that noise as "a noise-lingering time".

Thick solid lines shown in portions (a) to (c) of FIG. 9 indicate the timing with which periodic noises are mixed. In portions (a) to (c) of FIG. 9, the timing with which periodic noises are mixed is the timing of pulsation.

The timing with which periodic noises are mixed can be determined by, for example, determining a pulsation period from previously-measured cardiac pulses, and calculating the point of occurrence of each next cardiac pulse based on the determined period.

In portions (a) to (c) of FIG. 9, durations DN2 of about 250 ms from noise mixing are shown crosshatched. Each duration DN2 of about 250 ms from noise mixing is a span of time (noise-lingering time) during which the electroencephalogram is affected by the noise, as described above. However, this period of about 250 ms is only an example of noise-lingering time, which may fluctuate depending on the electrical device that is the noise source, etc.

The noise-lingering time is defined as a period from the timing with which a periodic noise is mixed until a point at which a predetermined time has just elapsed. Note that a predetermined duration DN1 (e.g. 100 ms) before the noise mixing, shown hatched, may also be included in the noise-lingering time, thus to accommodate a prediction error of timing with which periodic noises may be mixed.

In the UCL estimation using event-related potential, the accuracy of UCL estimation can be improved by presenting sound stimulations in such a manner that noise influence is not exerted in the valid period after each sound stimulation.

For example, sound stimulations may be presented so that the respective noise-lingering times do not overlap the measuring durations of event-related potentials in response to the second sound and third sound, which are found by the inventors to be valid for UCL estimation. Alternatively, a sound stimulation may be presented so that the noise-lingering time does not overlap the measuring duration of an event-related potential after the sound stimulation of the third sound (S3), which is especially valid, is presented. As a result, the accuracy of uncomfortable sound pressure estimation can be improved. Hereinafter, this will be described more specifically.

The measuring durations of event-related potentials in response to the second sound and third sound within a plurality of sound stimulations being presented may be regarded as analysis-pertinent zones. In portions (a) to (c) of FIG. 9, analysis-pertinent zones DI are shown in gray. In portions (a) and (b) of FIG. 9, only the measuring duration of an event-related potential in response to the third sound is set as an analysis-pertinent zone DI. The analysis-pertinent zone DI can be defined as a predetermined duration after a sound stimulation is generated.

Sound stimulations are generated so that any analysis-pertinent zone DI extends after the noise-lingering time DN2 has elapsed since a point of noise occurrence (i.e., so as to avoid overlap between the noise-lingering time DN2 and the analysis-pertinent zone DI). To this end, information of the intervals between the first sound, second sound, and third sound (inter-stimulation time information), and the measuring duration of an event-related potential after each sound stimulation generation (the amount of time after a stimulation until measurement) are previously determined, for example. Note that the event-related potential may be constantly measured, and information of the measuring duration of an event-related potential after each sound stimulation generation may be extracted from the electroencephalogram thus measured.

In the case where the measuring durations of event-related potentials in response to the second sound and third sound are to be regarded as analysis-pertinent zones (e.g., as shown in a portion (c) of FIG. 9), sound stimulations may be generated so that period A and period B (described below) end at the same point in time, for example. It is not necessary that period A and period B end at the same point in time; period B may end after period A ends.

Period A is a period after a point of noise occurrence until the noise-lingering time elapses. Period B is a period from a point of presenting the first sound until a point of presenting the second sound. Alternatively, period B may be a period from a point of presenting the first sound until a point at which measurement of the event-related potential in response to the first sound is ended.

On the other hand, in the case where only the measuring duration of an event-related potential in response to the third sound is to be regarded as an analysis-pertinent zone (e.g., as shown in portions (a) and (b) of FIG. 9), period B may be a period from a point of presenting the first sound until a point at which the measuring duration of an event-related potential after the second sound is presented is ended, for example. In this case, the length of period B is a sum of the lengths of sound stimulations of the first and second sounds, the interval between the first sound and the second sound, and the measuring duration of the event-related potential after the second sound generation (i.e., the time from the stimulation until the measurement).

In the case where periodic noises are mixed at a period shorter than 1.7 Hz, it is possible that the zone of low noise influence may be shorter than the analysis-pertinent zone, i.e., 300 ms. In other words, it is possible that the measuring duration of the event-related potential after the second sound generation may overlap the next point of noise occurrence.

In that case, sound stimulations may be presented in such a manner that the zone of 150 to 200 ms after S3 presentation, which is the most important zone (third sound) among the analysis-pertinent zones (second sound and third sound), fits within the zone of low noise influence.

Hereinafter, estimation of points of noise occurrence will be described.

A portion (b) of FIG. 8 shows the timing with which periodic noises occur with pulsation. Any point in time at which a result of subjecting the measured electroencephalogram to differentiation exceeds a predetermined threshold value may be detected as a point in time at which noise has occurred.

The timing of next periodic noise occurrence can be determined from the occurrence interval between past periodic noises.

For example, it may be determined by adding an average value of the occurrence intervals of ten immediately-previous periodic noises to the timing of final periodic noise occurrence. The occurrence interval may be determined through weighted averaging of the occurrence intervals of immediately previous periodic noises. Furthermore, in the case where the heart rate is higher than the heart rate of the ordinary user of the same age and sex as the user, the occurrence interval which has been determined by the above method may be corrected by being multiplied by a predetermined attenuation factor.

Generally speaking, periodic noises associated with pulsation tends to become stabilized over time, when at rest. On the other hand, there may be users whose pulsation period fluctuates, rather than being stable, for reasons such as illness. Therefore, the breadth of fluctuations in the interval between periodic noises associated with the user's pulsation, and the fluctuation tendency (i.e., whether it is an increase or a decrease), may be calculated to determine whether the period fluctuates over time or not.

In the case where the period fluctuates beyond a predetermined breadth over time, start of the electroencephalogram measurement may be delayed so as to avoid the influence of periodic noises.

In the case where the period does not fluctuate beyond the predetermined breadth over time, a process of increasing the number of summations, etc., may be additionally introduced in order to reduce the influence of periodic noises, without changing the time of measurement of the electroencephalogram.

The predetermined breadth can be determined from a standard deviation of the interval between periodic noises which would occur in an ordinary user. For example, if an ordinary user in stable state has a standard deviation of 0.1 s concerning the occurrence interval between periodic noises, then the predetermined breadth may be set to 0.1. Alternatively, the predetermined breadth may be set to equal to or less than three times a standard deviation that covers essentially any and all users in stable state. In the case where the interval between periodic noises keeps fluctuating beyond the predetermined breadth, a prediction error margin as broad as e.g. 200 ms may be allowed for the next periodic noise occurrence.

In the case where the interval between periodic noises is fluctuating for reasons other than illness and the like, it is presumable that the period will eventually become stable. Therefore, when such a user exhibits a tendency that the period of his or her periodic noises fluctuate over time, it should be possible to determine how soon a stable electroencephalogram measurement will become available. Presenting such time information to a person who takes the measurements will enable effective use of the time which the person spends for explaining about the measurement to the user, and making the preparations.

Figure 15:
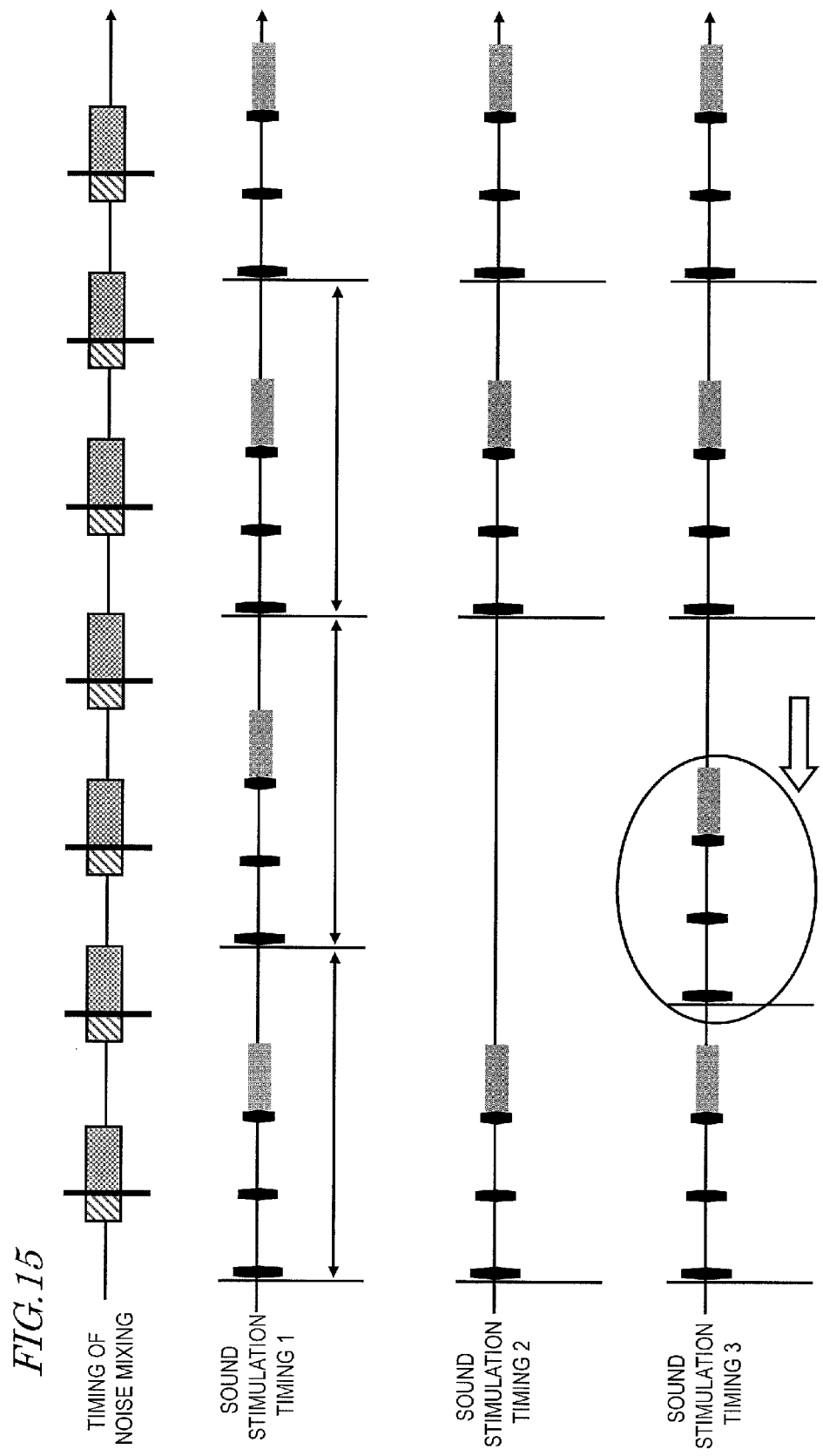
FIG. 15 is a diagram showing an exemplary method of presenting stimulations.

Examples of determining a schedule of timing for presenting sound stimulations based on the relationship between zones of low noise influence and analysis-pertinent zones has been described above. As the period of periodic noises becomes shorter, zones of low noise influence decrease in length. In an ordinary user in stable state, the period of periodic noises associated with pulsation or the like has a small variance. Therefore, when the pulsation frequency is high and the period of periodic noises is short, there is reduced freedom as to the sound stimulation timing for setting analysis-pertinent zones to fall within the zones of low noise influence. This forces the sound stimulations to occur at constant timing, as in stimulation timing 1 shown in FIG. 15, thus leading to a problem of taming (habituation) in event-related potential measurement. Possible methods of scheduling are, for example, omitting certain stimulations, as in sound stimulation timing 2 shown in FIG. 15; or shifting the timing of certain sound stimulations forward or rearward, as in sound stimulation timing 3 show in FIG. 15. However, when the timing of a sound stimulation is shifted, the analysis-pertinent zone may no longer fall within the zone of low noise influence. In this case, the corresponding measurement result may be ignored from analysis.

In outline, an embodiment of the present invention for realizing the above-described uncomfortable sound pressure estimation is as follows.

An uncomfortable sound pressure estimation system according to an embodiment of the present invention comprises: a biological signal measurement section for measuring an electroencephalogram signal of a user; an output section for presenting a sound stimulation group including a first sound, a second sound, and a third sound to the user, the first sound, the second sound, and the third sound having a same frequency and having sound pressures in a predetermined range; a characteristic amount extraction section for, from the electroencephalogram signal in a predetermined analysis zone defined based on a point of presenting at least one of the second sound and the third sound to the user as a starting point, extracting a characteristic amount of event-related potential associated with at least one of the second sound and the third sound; a determination section for determining an uncomfortable sound pressure for the frequency of the sound stimulation group, based on the characteristic amount extracted by the characteristic amount extraction section; a periodic noise extraction section for, from the electroencephalogram signal of the user, extracting a point of occurrence of at least one of a plurality of noises constituting periodic noises; a noise occurrence prediction section for predicting a next point of noise occurrence from the point of occurrence of the at least one noise extracted by the periodic noise extraction section; and a sound stimulation scheduling section for determining an output timing for the sound stimulation group so that an analysis zone for at least one of the second sound and third sound begins after a predetermined time has elapsed since the predicted next point of noise occurrence.

The output section may output the first sound, the second sound, and the third sound so as to consecutively decrease in sound pressure.

The characteristic amount extraction section may extract an N1-P2 amplitude or a wavelet-coefficient related characteristic amount.

The periodic noise extraction section may subject the electroencephalogram signal of the user to differentiation, and if a result of the differentiation is equal to or greater than a predetermined threshold value, determine that noise has occurred.

The noise occurrence prediction section may calculate a period of periodic noise occurrences, and based on an average value or weighted average value of occurrence intervals between a past plurality of points of noise occurrence, predict a next point of noise occurrence.

The sound stimulation scheduling section may set an output timing for the sound stimulation group so that the analysis zone does not fall into a time slot which begins from 100 ms before the next point of noise occurrence predicted by the noise occurrence prediction section and spans 250 ms, the analysis zone being a zone from 0 ms to 300 ms after the third sound is output.

The uncomfortable sound pressure estimation system may further comprise: a sound stimulation group determination section for determining the frequency of the sound stimulation group including the first sound, the second sound, and the third sound, each sound being a pure tone; and a sound stimulation sound pressure determination section for determining the sound pressures of the first sound, the second sound, and the third sound so that the first sound, the second sound, and the third sound consecutively decrease in sound pressure in this order while being equal to or less than a predetermined threshold value, wherein the output section outputs the first sound, the second sound, and the third sound at the frequency determined by the sound stimulation group determination section and at the sound pressures determined by the sound stimulation sound pressure determination section.

By referring to a time interval between the first sound and the second sound, the sound stimulation scheduling section may determine the points in time of outputting the first sound, the second sound, and the third sound so that times of measurement for event-related potentials in response to the second sound and third sound arrive after a predetermined noise-lingering time has elapsed since the next point of noise occurrence predicted by the noise occurrence prediction section.

The sound stimulation scheduling section may determine the points in time of outputting the first sound, the second sound, and the third sound so that, if a time interval with which the periodic noises have occurred is shorter than a time from a point of beginning measurement of the event-related potential in response to the second sound till a point of ending measurement of the event-related potential in response to the third sound, the analysis zone for the third sound begins after a predetermined noise-lingering time has elapsed since the next point of noise occurrence predicted by the noise occurrence prediction section.

An uncomfortable sound pressure estimation apparatus according to an embodiment of the present invention comprises: a sound stimulation scheduling section for receiving a next point of noise occurrence predicted based on a time interval with which periodic noises occur, the time interval being obtained from an electroencephalogram signal of a user measured by a biological signal measurement section for measuring an electroencephalogram signal of the user, and based on a previously-retained interval between a first sound, a second sound, and a third sound, determining points in time of outputting the first sound, the second sound, and the third sound so that times of measurement for event-related potentials in response to the second sound and third sound arrive after a predetermined noise-lingering time has elapsed since the predicted next point of noise occurrence; a characteristic amount extraction section for receiving the points in time of outputting the first sound, the second sound, and the third sound determined by the sound stimulation scheduling section, and, from the electroencephalogram signal of the user measured by the biological signal measurement section, extracting a characteristic amount of an event-related potential of the electroencephalogram signal based on the point in time of outputting each of the first sound, the second sound, and the third sound as a starting point; and a determination section for determining an uncomfortable sound pressure for a frequency of the sound stimulation group, based on the characteristic amounts extracted by the characteristic amount extraction section.

An uncomfortable sound pressure estimation system according to another embodiment of the present invention comprises: a biological signal measurement section for measuring an electroencephalogram signal of a user; an output section for presenting a sound stimulation to the user; a characteristic amount extraction section for extracting a characteristic amount of an event-related potential associated with the sound stimulation, from the electroencephalogram signal in a predetermined analysis zone defined based on a point in time of presenting the sound stimulation as a starting point; an uncomfortable sound pressure determination section for determining an uncomfortable sound pressure for a frequency of the sound stimulation group, based on the characteristic amount extracted by the characteristic amount extraction section; a periodic noise extraction section for, from the electroencephalogram signal of the user, extracting a point of occurrence of at least one of a plurality of noises constituting periodic noises; a noise occurrence prediction section for predicting a next point of noise occurrence from the point of occurrence of the at least one noise extracted by the periodic noise extraction section; and a sound stimulation scheduling section for determining an output timing for the sound stimulation, based on the next point of noise occurrence predicted by the noise occurrence prediction section.

An uncomfortable sound pressure estimation method according to an embodiment of the present invention comprises: a first biological signal measuring step of measuring an electroencephalogram signal of a user; a noise extracting step of, from the electroencephalogram signal of the user measured by the first biological signal measuring step, extracting a point of occurrence of at least one of a plurality of noises constituting periodic noises; a noise occurrence predicting step of predicting a next point of noise occurrence from the point of occurrence of the at least one noise extracted by the noise extracting step; a sound stimulation scheduling step of, prior to presenting a sound stimulation group including a first sound, a second sound, and a third sound to the user, the first sound, the second sound, and the third sound having a same frequency and sound pressures in a predetermined range, determining an output timing for the sound stimulation group so that an analysis zone for at least one of the second sound and third sound begins after a predetermined time has elapsed since the predicted next point of noise occurrence; an outputting step of, with the output timing determined by the sound stimulation scheduling step, presenting to the user the sound stimulation group including the first sound, the second sound, and the third sound having the same frequency and sound pressures in the predetermined range; a second biological signal measuring step of measuring an electroencephalogram signal of the user when the sound stimulation group is presented with the output timing in the outputting step; a characteristic amount extracting step of, from the electroencephalogram signal measured by the second biological signal measuring step in a predetermined analysis zone defined based on a point in time of presenting at least one of the second sound and the third sound to the user as a starting point, extracting a characteristic amount of an event-related potential associated with at least one of the second sound and the third sound; and an uncomfortable sound pressure determining step of determining an uncomfortable sound pressure for the frequency of the sound stimulation group, based on the characteristic amount extracted by the characteristic amount extracting step.

A computer program according to an embodiment of the present invention is a computer program to be executed by a computer mounted in an uncomfortable sound pressure estimation apparatus of an uncomfortable sound pressure estimation system, wherein the computer program causes the computer to execute: a first biological signal measuring step of acquiring an electroencephalogram signal of a user; a noise extracting step of, from the electroencephalogram signal of the user acquired by the first biological signal measuring step, extracting a point of occurrence of at least one of a plurality of noises constituting periodic noises; a noise occurrence predicting step of predicting a next point of noise occurrence from the point of occurrence of the at least one noise extracted by the noise extracting step; a sound stimulation scheduling step of, prior to presenting a sound stimulation group including a first sound, a second sound, and a third sound to the user, the first sound, the second sound, and the third sound having a same frequency and sound pressures in a predetermined range, determining an output timing for the sound stimulation group so that an analysis zone for at least one of the second sound and third sound begins after a predetermined time has elapsed since the predicted next point of noise occurrence; an outputting step of, with the output timing determined by the sound stimulation scheduling step, presenting to the user the sound stimulation group including the first sound, the second sound, and the third sound having the same frequency and sound pressures in the predetermined range; a second biological signal measuring step of acquiring an electroencephalogram signal of the user when the sound stimulation group is presented with the output timing in the outputting step; a characteristic amount extracting step of, from the electroencephalogram signal acquired by the second biological signal measuring step in a predetermined analysis zone defined based on a point in time of presenting at least one of the second sound and the third sound to the user as a starting point, extracting a characteristic amount of an event-related potential associated with at least one of the second sound and the third sound; and an uncomfortable sound pressure determining step of determining an uncomfortable sound pressure for the frequency of the sound stimulation group, based on the characteristic amount extracted by the characteristic amount extracting step.

(Embodiment 1)

First, the construction and operation of an uncomfortable sound pressure estimation system according to Embodiment 1 will be described.

Figure 10:
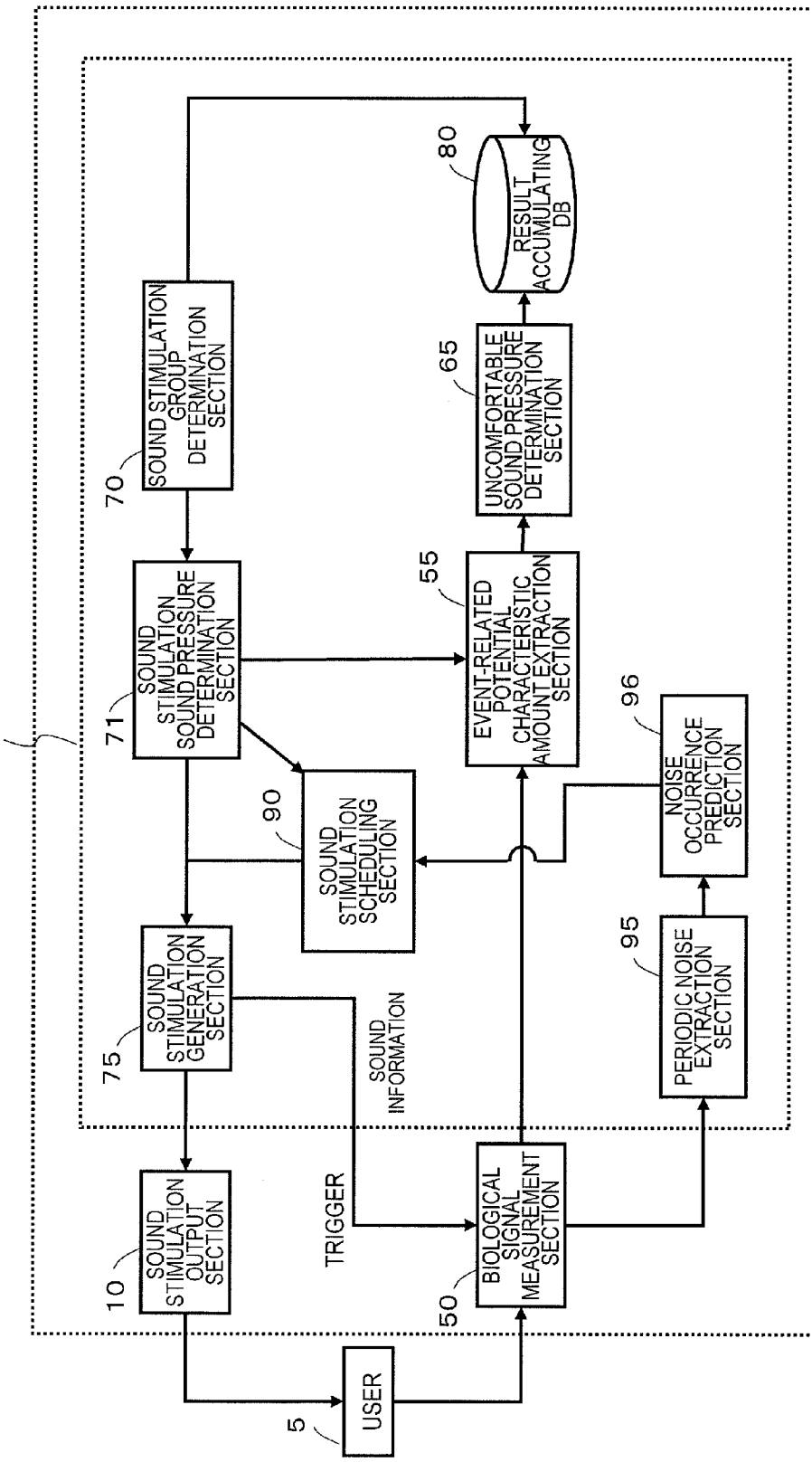
FIG. 10 is a diagram showing an exemplary construction of the uncomfortable sound pressure measurement system of Embodiment 1.

FIG. 10 shows the functional block construction of the uncomfortable sound pressure estimation system 100 according to the present embodiment.

The uncomfortable sound pressure estimation system 100 (which hereinafter may be referred to as the "estimation system 100") includes a sound stimulation output section 10, a biological signal measurement section 50, and an uncomfortable sound pressure estimation apparatus 1. The uncomfortable sound pressure estimation apparatus 1 (which hereinafter may be referred to as the "estimation apparatus 1") includes an event-related potential characteristic amount extraction section 55, an uncomfortable sound pressure determination section 65, a sound stimulation group determination section 70, a sound stimulation sound pressure determination section 71, a sound stimulation generation section 75, a result accumulating DB 80, a sound stimulation scheduling section 90, a periodic noise extraction section 95, and a noise occurrence prediction section 96. In the following, the event-related potential characteristic amount extraction section 55 may be referred to as the "characteristic amount extraction section 55"; the uncomfortable sound pressure determination section 65 as the "determination section 65"; and the sound stimulation sound pressure determination section 71 as the "sound pressure determination section 71".

The estimation apparatus 1 is connected to the sound stimulation output section 10 and the biological signal measurement section 50 in a wired or wireless manner. The sound stimulation output section 10 is constructed so as to present sound stimulations to the user 5, whereas the biological signal measurement section 50 is constructed so as to measure a biological signal of the user 5. For conciseness of explanation, the user 5 block is also shown in the figure.

The construction of the estimation apparatus 1 shown in FIG. 10 is an example. The estimation apparatus 1 may at least include the characteristic amount extraction section 55, the uncomfortable sound pressure determination section 65, and the sound stimulation scheduling section 90. The estimation apparatus 1 may be constructed to include the sound stimulation output section 10, for example.

For example, the estimation system 100 of the present embodiment presents pure tones in a sound pressure range that is higher than the HTL and lower than a sound pressure which is generally evaluated to be the UCL at monotonously descending sound pressures, totaling three times in succession in time slots that are unlikely to be affected by periodic noises, and extracts electroencephalographic characteristic amounts to the respective sound stimulations of first to third sounds, and measures an uncomfortable sound pressure from the change pattern in the characteristic amounts.

<Environment of Use>

Figure 11:
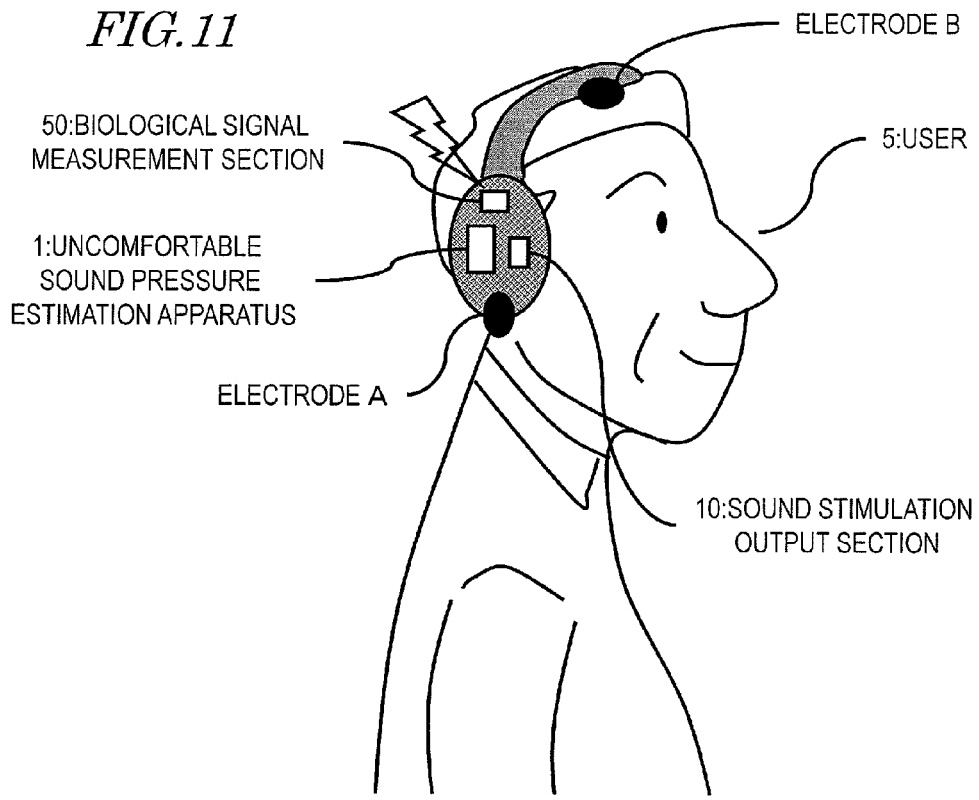
FIG. 11 is a diagram showing an exemplary environment of use for the uncomfortable sound pressure estimation system of Embodiment 1.

FIG. 11 shows a construction and an environment of use for the uncomfortable sound pressure estimation system 100 of the present embodiment. The estimation system 100 corresponds to the system construction of Embodiment 1 shown in FIG. 10. The estimation system 100 includes the estimation apparatus 1, the sound stimulation output section 10, and the biological signal measurement section 50.

<Sound Stimulation Output Section 10>

The sound stimulation output section 10 outputs sound stimulations to the user 5. The sound stimulation output section 10 may be headphones or a loudspeaker whose frequency characteristics are free of distortion, for example.

To the user 5, the sound stimulation output section 10 outputs sound stimulation data which is generated by the estimation apparatus 1 (sound stimulation generation section 75). Preferably the sound stimulation output section 10 is capable of separately outputting to each of the right and left ears a sound stimulation which is generated by the estimation apparatus 1 (sound stimulation generation section 75). Hereinafter, the sound stimulation output section 10 will also be referred to as the "output section".

<Biological Signal Measurement Section 50>

<The biological signal measurement section50>is a measuring instrument for measuring a biological signal of the user 5. In the present disclosure, the biological signal measurement section 50 is an electroencephalograph. The biological signal measurement section 50 measures an electroencephalogram corresponding to a potential difference between a probe electrode B and a reference electrode A worn by the user 5.

The probe electrode B is placed at an electrode position complying with the International 10-20 system (10-20 System) shown in FIG. 3A, for example. The reference electrode A is placed at the mastoid of the user 5, for example.

Note that the level (amplitude level) and polarity (the amplitude being plus or minus) of a characteristic component of the event-related potential may possibly vary depending on the sites at which electrodes for electroencephalogram measurement are worn, and on the positions at which the reference electrode and the probe electrode are set.

However, based on the following description, those skilled in the art should be able to extract a characteristic feature of the event-related potential and perform an uncomfortable sound pressure measurement by making appropriate modifications in accordance with the particular reference electrode and probe electrode used. Such variants are encompassed within the present disclosure.

The electroencephalogram data may be subjected to frequency filtering with an appropriate cutoff frequency. The biological signal measurement section 50 sends measured electroencephalogram or the filtered electroencephalogram to the estimation apparatus 1 (the periodic noise extraction section 95 and the characteristic amount extraction section 55). Hereinafter, a measured or filtered electroencephalogram may also be referred to as "electroencephalogram data".

For example, the electroencephalogram data may be subjected to frequency filtering with an appropriate cutoff frequency, and, together with trigger information which is received from the estimation apparatus 1 (the sound stimulation generation section 75), sent to the estimation apparatus 1 (the periodic noise extraction section 95 and the characteristic amount extraction section 55).

In the case where a band-pass filter is used as the frequency filter, the cutoff frequency may be set so as to pass e.g. 5 Hz to 15 Hz. It is assumed that the user 5 has worn the electroencephalograph in advance. The probe electrode for electroencephalogram measurement is attached at the central portion Cz, for example.

<Uncomfortable Sound Pressure Estimation Apparatus 1>

The estimation apparatus 1 determines the information of a plurality of sound stimulations to be output to the user 5. Specifically, it determines points in time to output a plurality of sound stimulations in such a manner that the time of measuring an event-related potential in an analysis-pertinent zone does not coincide with the time of a periodic noise. Determination of points in time to output a plurality of sound stimulations may also be referred to as "scheduling of sound stimulations".

An analysis-pertinent zone is, given a continuum of event-related potential in response to a plurality of sound stimulations, any zone that is valid for uncomfortable sound pressure estimation. According to the finding of the inventors described above, in the case where the plurality of sound stimulations are a first sound, a second sound, and a third sound, it is preferable that the periods during which event-related potential in response to the second sound and third sound (in particular, an event-related potential to the third sound) is obtained are set as analysis-pertinent zones.

The sound stimulations which are determined by the estimation apparatus 1 are presented to the user 5 by the sound stimulation output section 10.

The estimation apparatus 1 extracts a characteristic amount of the event-related potential that has been cut out based on the point of presenting each of the plurality of sound stimulations as a starting point. Within the event-related potential in response to a plurality of sound stimulations, an uncomfortable sound pressure is to be estimated based on the event-related potential in an analysis-pertinent zone(s). The uncomfortable sound pressure is preferably estimated for each ear (right or left ear) of the user and for each sound frequency, for example. The details will be described later.

In the estimation system 100 shown in FIG. 11, the estimation apparatus 1, the biological signal measurement section 50, and the sound stimulation output section 10 are accommodated in the same housing.

The biological signal measurement section 50 and the sound stimulation output section 10 of the estimation system 100 may be provided in a separate housing from the estimation apparatus 1. In that case, an electroencephalogram signal measured by the biological signal measurement section 50 is sent to the estimation apparatus 1, which is connected in a wireless or wired manner.

<Hardware Construction of the Uncomfortable Sound Pressure Estimation Apparatus 1>

Figure 12:
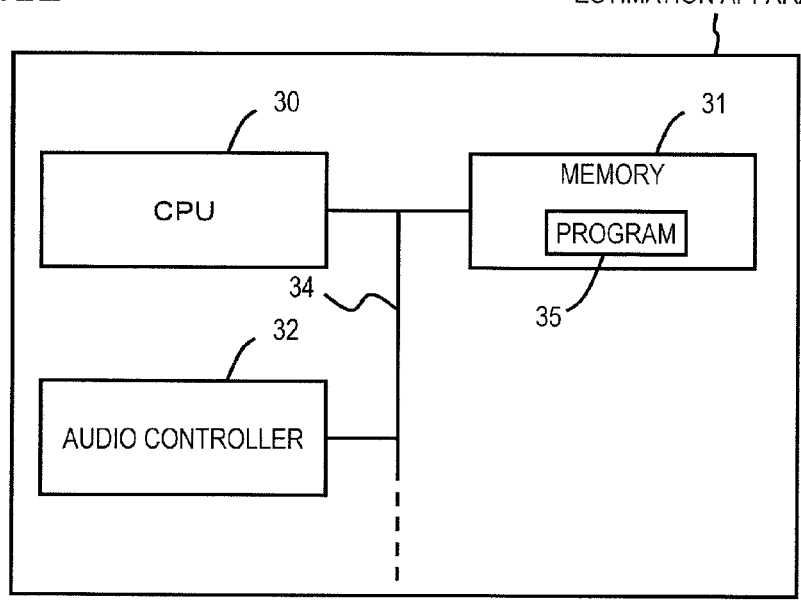
FIG. 12 is a diagram showing an exemplary hardware construction according to Embodiment 1.

FIG. 12 shows an exemplary hardware construction of the uncomfortable sound pressure estimation apparatus 1 of the present embodiment.

The estimation apparatus 1 is composed of the CPU 30, a memory 31, and an audio controller 32. The CPU 30, the memory 31 (storage medium), and the audio controller 32 are interconnected via a bus 34, so that data exchange among them is possible. The respective component elements of the estimation apparatus 1 are implemented by the CPU 30.

The CPU 30 executes a computer program 35 which is stored in the memory 31. A processing procedure as illustrated by a subsequently-described flowchart is described in the computer program 35. In accordance with the computer program 35, the estimation apparatus 1 performs processes of controlling the entire estimation system 100, such as generation of sound stimulations, extraction and predict of periodic noises, extraction of characteristic amounts of event-related potentials, and discriminant analysis for uncomfortable sound pressure determination. These processes will be described in detail later.

In accordance with instructions from the CPU 30, the audio controller 32 outputs the sound stimulations for presentation via the sound stimulation output section 10 at designated sound pressures.

Note that the estimation apparatus 1 may be implemented as a piece of hardware (e.g., a DSP) consisting of a semiconductor circuit having a computer program incorporated therein. Such a DSP can realize all functions of the aforementioned CPU 30, memory 31, and audio controller 32 on a single integrated circuit.

The aforementioned computer program 35 may be distributed on the market in the form of a product recorded on a storage medium such as a CD-ROM, or transmitted through telecommunication lines such as the Internet. Upon reading the computer program 35, a device having the hardware shown in FIG. 12 (e.g., a PC) is able to function as the uncomfortable sound pressure estimation apparatus 1 according to the present embodiment.

The respective functional blocks of the estimation apparatus 1 correspond to functions which are realized by the CPU 30, the memory 31, and the audio controller 32 as a whole upon executing the program which has been described in conjunction with FIG. 12.

Hereinafter, the respective component elements of the estimation apparatus 1 will be described.

<Sound Stimulation Group Determination Section 70>

The sound stimulation group determination section 70 determines the information of a plurality of sound stimulations (sound stimulation group) to be presented to the user 5. In the present embodiment, the sound stimulation group at least contains a first sound, a second sound, and a third sound.

Preferably, the information of the sound stimulation group includes frequency of the sound stimulation group. It is preferable that the first sound, second sound, and third sound have the same frequency. In the present specification, "same frequency" is inclusive of not only a completely equal frequency, but also of frequencies sharing a difference that is smaller than the precision with which humans can aurally distinguish. For example, frequencies with a difference of 5 Hz or less are regarded as the same frequency.

The information of the sound stimulation group may contain the ear to which the sound stimulations are to be presented (the right ear or the left ear), the frequencies of the sound stimulations to be presented, the duration of the sound stimulations within the sound stimulation group, and the interval between the plurality of sound stimulations.

The sound stimulation group determination section 70 may randomly decide the frequency and the ear for which to present the sound stimulation under the following constraints, for example. Preferably, a sound stimulation group of a different frequency from that of an immediately previous sound stimulation group is selected. The ear is preferably selected in random order between right and left; however, it is preferable that not more than four sound stimulation groups are successively presented to either the right or left ear. Thus, the influence of taming (habituation) of the electroencephalogram due to successive presentation of sound stimulation groups to the same ear and with the same frequency is reduced, whereby uncomfortable sound pressure estimation can be realized with a high precision.

The duration of a sound stimulation may be set to e.g. 25 ms or more, so that an auditory evoked potential will be stably induced. Moreover, the interval between successive sound stimulations is set to a time which is equal to or greater than the duration of a sound stimulation and equal to or less than 1 second, e.g., 300 ms or 200 ms.

The sound stimulation group determination section 70 sends the information of the plurality of sound stimulations thus determined to the sound stimulation sound pressure determination section 71 or the sound stimulation generation section 75.

<Sound Stimulation Sound Pressure Determination Section 71>

The sound pressure determination section 71 determines the sound pressures of the group of plural sound stimulations so that the sound pressures fall in a range which is equal to or less than a predetermined sound pressure and consecutively decrease in a monotonous manner.

The range which is equal to or less than a predetermined sound pressure is, for example, a sound pressure range that is greater than a previously-known HTL of the user 5 and smaller than a sound pressure which is generally evaluated to be the UCL.

The sound pressure determination section 71 sets the sound pressures of the group of plural sound stimulations to less than a sound pressure which is generally evaluated to be the UCL (threshold value), for example. In other words, it sets the sound pressures of the sound stimulations in the sound stimulation group (e.g., first to third sounds) to be in a sound pressure range which can be comfortably heard by the user 5. The sound pressure determination section 71 may previously retain a predetermined threshold value.

For example, assuming that the HTL value at a given frequency is 50 dBHL, and the predetermined sound pressure is 90 dBHL, then the sound pressure of the first sound may be determined as 80 dBHL, the sound pressure of the second sound as 75 dBHL, and the sound pressure of the third sound as 70 dBHL.

As mentioned above, "monotonously descending" means that each next sound has an equal or smaller sound pressure as compared to its preceding sound. In the case where the sound stimulation group consists of a first sound, a second sound, and a third sound, the sound pressures are to be determined so that the following relationship is satisfied: sound pressure of first sound>sound pressure of second sound>sound pressure of third sound.

Moreover, the sound pressure determination section 71 sends the interval between sound stimulations in the sound stimulation group to the sound stimulation scheduling section 90.

<Periodic Noise Extraction Section 95>

Receiving an electroencephalogram of the user 5 from the biological signal measurement section 50, the periodic noise extraction section 95 performs extraction of periodic noises.

For example, in the case where noise associated with a pacemaker is to be extracted as periodic noises, the electroencephalogram received from the biological signal measurement section 50 is subjected to differentiation, whereby any point in time at which an electroencephalogram that is greater than a predetermined threshold value occurs can be detected as the timing of periodic noise occurrence.

The aforementioned predetermined threshold value may be determined based on the sampling frequency, time constant, or an analog low-pass filter of the biological signal measurement section 50. Under a sampling frequency of 1000 Hz, a time constant of 1 second, and a 60 Hz low-pass filter, the predetermined threshold value may be 10, for example. The periodic noise extraction section 95 sends the extracted information of timing of periodic noise occurrence to the noise occurrence prediction section 96.

<Noise Occurrence Prediction Section 96>

The noise occurrence prediction section 96 predicts the timing of a next-occurring periodic noise to be mixed in the electroencephalogram. The timing of next periodic noise occurrence can be determined from the occurrence interval between past periodic noises. For example, it may be determined by adding an average value of the occurrence intervals of ten immediately-previous periodic noises to the timing of final periodic noise occurrence.

The noise occurrence interval may be determined through weighted averaging of the occurrence intervals of immediately previous periodic noises. Furthermore, in the case where the heart rate is higher than the heart rate of the ordinary user of the same age and sex as the user, the occurrence interval which has been determined by the above method may be corrected by being multiplied by a predetermined attenuation factor. Then, the predicted timing of next periodic noise occurrence (point in time) is sent to the sound stimulation scheduling section 90.

<Sound Stimulation Scheduling Section 90>

The sound stimulation scheduling section 90 determines points in time of presenting the plurality of sound stimulations so that the analysis-pertinent zone(s) does not coincide with any of the periods during which the periodic noises are occurring (noise-lingering time).

The analysis-pertinent zone is, in the case where the plurality of sound stimulations consists of a first sound, a second sound, and a third sound, time slots after the second sound and third sound are presented (periods during which event-related potentials in response to the second sound and third sound are measured), for example. The analysis-pertinent zone may be predetermined periods after the second sound and third sound are output, or a predetermined period as reckoned from a point in time after a predetermined time has just elapsed since the second sound and third sound were output.

The sound stimulation scheduling section 90 may determine an analysis-pertinent zone(s) by referring to the intervals between the respectively stimulations of the first sound, and second sound, and third sound, and predetermined amounts of time after the second sound and the third sound are output. Alternatively, a predetermined time corresponding to the time after the first sound is output until the times of measurement of the event-related potentials in response to the second sound and third sound may be previously retained, and an analysis-pertinent zone(s) may be determined on that basis.

The sound stimulation scheduling section 90 acquires the information of the occurrence interval of periodic noises, the points of occurrence of periodic noises, and the noise-lingering time, for example, and determines points in time to output the plurality of sound stimulations so that the analysis-pertinent zone(s) does not coincide with the noise-lingering time beginning from any point of occurrence of noise.

The span of time from a point of noise occurrence until the noise-lingering time has just elapsed may also be referred to as a "noise zone". The span of time which begins when the noise-lingering time has just elapsed since a point of noise occurrence and lasts until a next noise occurrence may also be referred to as a "zone of low noise influence".

As to the analysis-pertinent zone(s), it is preferable that the time of measurement of an event-related potential in response to the third sound, in particular, does not coincide with a noise zone. If a total time of measurement of event-related potentials in response to the second sound and third sound is longer than a zone of low noise influence, the sound stimulation scheduling section 90 may determine the points in time to output the plurality of sound stimulations so that the time of measurement of an event-related potential in response to the third sound, rather than the second sound, does not coincide with a noise zone.

Hereinafter, an exemplary method of determining the points in time to present the plurality of sound stimulations will be described.

The sound stimulation scheduling section 90 receives from the sound pressure determination section 71 the stimulation interval within the sound stimulation group, and receives from the noise occurrence prediction section 96 the information of a next point of occurrence of periodic noises.

The sound stimulation scheduling section 90 determines the timing of sound stimulation presentation so that the time slot (analysis-pertinent zone) from 0 ms to 300 ms since the third sound of the next sound stimulation group is presented is a zone of low noise influence.

The zone of low noise influence may be set to a period from a point of 250 ms since the most recent timing of periodic noise occurrence until a point 100 ms before the timing of next periodic noise occurrence, for example. The timing of next periodic noise occurrence is predicted by the noise occurrence prediction section 96, and notified to the sound stimulation scheduling section 90.

In the case where periodic noises are mixed with a higher frequency (shorter period) than 1.7 Hz, the zone of low noise influence may be shorter than the analysis-pertinent zone, i.e., 300 ms. In that case, the timing of sound stimulation presentation is to be determined so that the zone from 150 to 200 ms after S3 presentation, which is the most important of analysis-pertinent zones, falls into a zone of low noise influence.

In other words, in the case where the amount of time resulting from subtracting the noise-lingering time from the occurrence interval of periodic noises is smaller than the analysis-pertinent zone, the points in time of sound stimulation generation are to be determined so that the most vital analysis-pertinent zone does not coincide with a noise zone.

Note that what is described with reference to portions (a) to (c) of FIG. 9 is also an example of how the sound stimulation scheduling section 90 may determine the points in time to present the plurality of sound stimulations. The sound stimulation scheduling section 90 sends to the sound stimulation generation section 75 the determined presentation timing of the sound stimulations of the first to third sounds.

<Sound Stimulation Generation Section 75>

The sound stimulation generation section 75 generates sound stimulation data based on the information of the ear and frequency for which the sound stimulation group is to be presented, durations of sound stimulations in the sound stimulation group, interval of presentation, and sound pressure, this information being received from the sound pressure determination section 71. Each sound stimulation may be a tone burst sound with a rise and fall of 3 ms, for example. Then, with the presentation timing for the sound stimulation group received from the sound stimulation scheduling section 90, the sound stimulations are output to the user 5 via the sound stimulation output section 10. Moreover, at the timing of outputting sound stimulation, a trigger signal(s) is output to the biological signal measurement section 50. Note that, without outputting any trigger signal to the biological signal measurement section 50, the sound stimulation generation section 75 may only send the generated sound stimulation data to the sound stimulation output section 10.

The sound stimulation data may be generated in such a manner that a single piece of sound stimulation data is created for one sound stimulation group, from which a plurality of sound stimulations that undergo changes in sound pressure at a predetermined time interval are derived, for example. In that case, the trigger signal to be sent to the biological signal measurement section 50 may only be sent at the timing of presenting the first sound.

Note that the sound stimulation generation section 75 may include an input device, or be connected to an external input device. In this case, the user 5 or a person who tests the hearing of the user 5 is able to input desired information by using the input device, and the sound stimulation generation section 75 can generate sound stimulation by using the information received from the input device.

<Event-Related Potential Characteristic Amount Extraction Section 55>

Based on the electroencephalogram and trigger information received from the biological signal measurement section 50, the characteristic amount extraction section 55 cuts out an event-related potential waveform in a predetermined zone which is defined based on the trigger information as a starting point (e.g., a zone from 100 ms before the presentation of the first sound to 400 ms after the presentation of the third sound). Moreover, based on the information of sound stimulations received from the sound pressure determination section 71, the characteristic amount extraction section 55 calculates wavelet-coefficient related characteristic amounts in response to the first to third sounds.

The calculated characteristic amount and the sound stimulation information (right or left ear, frequency, sound pressure, etc.) are sent to the uncomfortable sound pressure determination section 65. The wavelet-coefficient related characteristic amounts may be determined as values resulting from taking an average over a predetermined range on each of the frequency axis and the time axis, for example. For example, an average may be taken over a frequency range from 5 Hz to 15 Hz on the frequency axis and over a time range of 50 ms on the time axis. For example, in order to determine a wavelet characteristic amount concerning the P2 component, a biological signal in a time range which begins from the point of sound stimulation presentation and spans 300 ms or less after a sound stimulation is presented may be used. So long as uncomfortable sound pressure estimation is possible, the ranges on the frequency axis and the time axis over which averaging is to be conducted for characteristic amount calculation may be arbitrarily set. In other words, the frequency range is not limited to 5 Hz to 15 Hz, and the time range is not limited to 50 ms; they may be finer or coarser.

Note that the characteristic amount extraction section 55 may calculate N1-P2 amplitude-related characteristic amounts respectively in response to the second sound and the third sound from the event-related potentials received from the biological signal measurement section 50. An N1-P2 amplitude may be determined as the absolute value of a difference between N1 amplitude and P2 amplitude. For example, the N1 amplitude may be a zone average potential, or a peak amplitude, from 50 ms to 150 ms after the presentation of each sound stimulation of the second and third sounds. For example, the P2 amplitude may be a zone average potential, or a peak amplitude, from 150 ms to 250 ms after the presentation of each sound stimulation.

<Uncomfortable Sound Pressure Determination Section 65>

The uncomfortable sound pressure determination section 65 determines an uncomfortable sound pressure of the user 5 by referring to the characteristic amounts in response to the first sound, second sound, and third sound that have been extracted by the characteristic amount extraction section 55, against a predetermined criterion which previously defines associations between characteristic amounts and uncomfortable sound pressure values. Note that the determination section 65 may determine the uncomfortable sound pressure of the user 5 by referring to a characteristic feature of an event-related potential measured in an analysis-pertinent zone, against a predetermined criterion.

Specifically, by using the characteristic amounts concerning the respectively time-frequency information (e.g., wavelet coefficient) of the first to third sounds, which are received from the characteristic amount extraction section 55, the determination section 65 determines the uncomfortable sound pressure. The determination section 65 may conduct a linear discrimination by using time-frequency information (e.g., wavelet characteristic amount) which is prepared in advance against a predetermined criterion.

The predetermined criterion means information which previously defines associations between characteristic amounts and uncomfortable sound pressure values. The predetermined criterion may be a table defining associations between wavelet characteristic amounts and uncomfortable sound pressure values, or a predetermined equation. The predetermined criterion is retained in the determination section 65 in advance.

The predetermined criterion may be training data for subjective UCL values, for example. The training data is generated from subjective UCL values and time-frequency information (e.g., wavelet characteristic amounts) which were measured in the aforementioned subjective report experiment and electroencephalogram measurement experiment being conducted in advance for at least two ore more other people.

Herein, the sound stimulation conditions concerning the sound pressures and the number of sound stimulations in the electroencephalogram measurement experiment when generating the training data need to identically conform to the pattern of changing stimulation sound pressure as determined by the sound pressure determination section 71. The training data may be retained so as to be itemized for each of the right or left ear and each frequency, as shown in FIG. 13, for example. In that case, based on the sound stimulation information received from the characteristic amount extraction section 55 (the right or left ear and frequency), the training data which is utilized for uncomfortable sound pressure estimation may be switched so that the right or left ear and frequency of the training data match the right or left ear and frequency of the one who is the subject of determination. Moreover, the training data may be switched according to the user's symptoms of hypacusia. For example, training data may be prepared and switched between general categories, e.g., conductive deafness and perceptive deafness. Also, training data may be prepared and switched according to the audiogram pattern, e.g., gradual low tone loss or gradual high tone loss. The uncomfortable sound pressure determination section 65 sends the determined uncomfortable sound pressure to the result accumulating DB 80.

<Result Accumulating DB 80>

The result accumulating DB 80 stores the uncomfortable sound pressure received from the uncomfortable sound pressure determination section 65 in associated with the right or left ear and each frequency as indicated by the sound stimulation group information received from the sound stimulation group determination section 70. FIG. 13 shows an example of data accumulation in the result accumulating DB 80. FIG. 13 illustrates a case where an uncomfortable sound pressure is accumulated with respect to each of the right or left ear and each frequency.

<Processing by the Uncomfortable Sound Pressure Estimation System 100>

Figure 14:
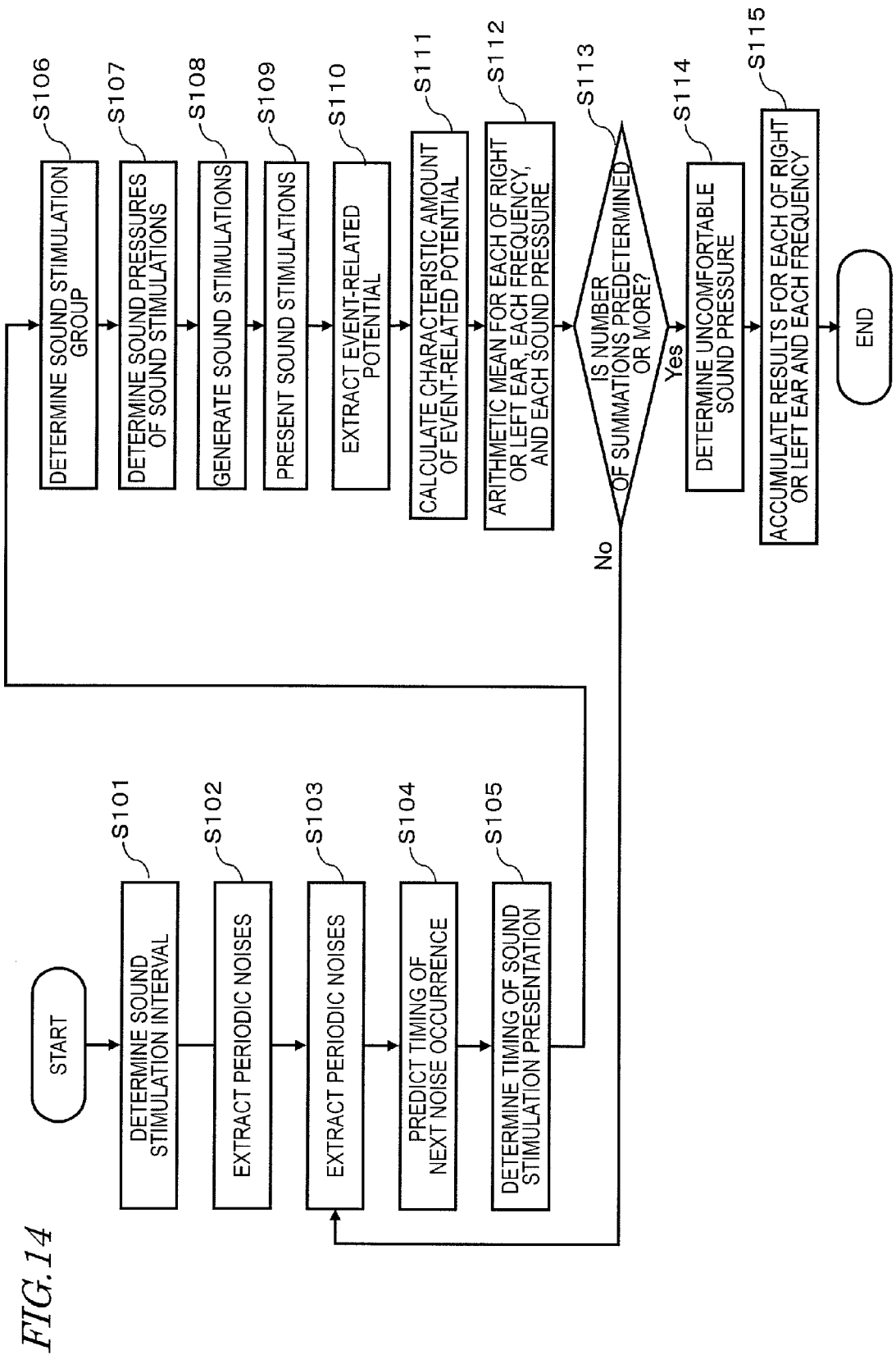
FIG. 14 is a flowchart showing overall processing by the uncomfortable sound pressure estimation system in outline.

Next, with reference to FIG. 14, a processing procedure which is performed by the estimation system 100 of FIG. 10 will be described. FIG. 14 is a flowchart showing a procedure of processing performed in the estimation system 100.

<Step S101>

The sound stimulation group determination section 70 determines the durations and interval of the sound stimulations to be presented to the user 5. The duration of each sound stimulation is set to e.g. 25 ms or more, so that auditory evoked potential will be stably induced. The interval between stimulations is set to be equal to or greater than the duration of each sound stimulation and equal to or less than 1 second, e.g., 300 ms or 200 ms. Then, these are sent to the sound stimulation scheduling section 90 via the sound stimulation sound pressure determination section 71.

<Step S102>

The biological signal measurement section 50 measures an electroencephalogram of the user 5 as a biological signal. Then, the electroencephalogram data is subjected to frequency filtering with an appropriate cutoff frequency, and sent to the noise extraction section 95 and the characteristic amount extraction section 55. Note that the electroencephalogram continues to be measured until step S115 (described later) is finished, during which time the electroencephalogram data is sent to the noise extraction section 95 and the characteristic amount extraction section 55. When trigger information is input to the biological signal measurement section 50, the trigger information is also sent to the characteristic amount extraction section 55.

<Step S103>

Receiving the electroencephalogram of the user 5 from the biological signal measurement section 50, the periodic noise extraction section 95 performs extraction of periodic noises. For example, in the case where noise associated with a pacemaker is to be extracted as periodic noises, the electroencephalogram received from the biological signal measurement section 50 is subjected to differentiation; and if a predetermined threshold value is exceeded, it is determined that periodic noises have occurred, and the timing of periodic noise occurrence is detected. The predetermined threshold value can be determined based on the sampling frequency, time constant, or an analog low-pass filter of the biological signal measurement section 50. Under a sampling frequency of 1000 Hz, a time constant of 1 second, and a 60 Hz low-pass filter, the predetermined threshold value may be 10, for example. Then, the extracted information of timing of periodic noise occurrence is sent to the noise occurrence prediction section 96.

<Step S104>

The noise occurrence prediction section 96 predicts the timing of a next-occurring periodic noise to be mixed in the electroencephalogram. The timing of next periodic noise occurrence can be determined from the occurrence interval between past periodic noises. For example, it may be determined by adding an average value of the occurrence intervals of ten immediately-previous periodic noises to the timing of final periodic noise occurrence. The occurrence interval may be determined through weighted averaging of the occurrence intervals of immediately previous periodic noises. Furthermore, in the case where the heart rate is higher than the heart rate of the ordinary user of the same age and sex as the user, the occurrence interval which has been determined by the above method may be corrected by being multiplied by a predetermined attenuation factor. Then, the predicted timing of next periodic noise occurrence (point in time) is sent to the sound stimulation scheduling section 90.

<Step S105>

The sound stimulation scheduling section 90 receives from the sound pressure determination section 71 the stimulation interval within the sound stimulation group, and receives from the noise occurrence prediction section 96 the information of a next point of occurrence of periodic noises. The sound stimulation scheduling section 90 determines the timing of sound stimulation presentation so that the time slot (analysis-pertinent zone) from 0 ms to 300 ms since the second sound and third sound (or the third sound alone) of the next sound stimulation group are presented is a zone of low noise influence. The zone of low noise influence may be set to a period from 250 ms since the most recent timing of periodic noise occurrence until 100 ms before the timing of next periodic noise occurrence received from the noise occurrence prediction section 96, for example. In the case where periodic noises are mixed with a shorter period than is defined by 1.7 Hz, the zone of low noise influence may be shorter than the analysis-pertinent zone, i.e., 300 ms. In that case, the timing of sound stimulation presentation is to be determined so that the zone from 150 to 200 ms after S3 presentation, which is the most important of analysis-pertinent zones, falls into a zone of low noise influence. Then, the sound stimulation scheduling section 90 sends to the sound stimulation generation section 75 the determined presentation timing of the sound stimulations of the first to third sounds.

<Step S106>

The sound stimulation group determination section 70 determines the ear and frequency for which the sound stimulation group is to be presented. The ear and frequency for which presentation is to be made may be randomly determined based on the following constraints, for example: no sound stimulation of the same frequency as that of an immediately previous sound stimulation group is selected; the ear is selected in random order between right and left; however, not more than four sound stimulation groups are successively presented to either the right or left ear.

<Step S107>

From the sound stimulation group determination section 70, the sound stimulation sound pressure determination section 71 receives the information of the ear and frequency for which the sound stimulation group is to be presented, durations of sound stimulations in the sound stimulation group, and interval between stimulations. Moreover, the sound stimulation sound pressure determination section 71 determines the sound pressures of the sound stimulation group so that the sound pressure falls in a sound pressure range that is greater than the previously-known HTL and lower than a sound pressure which is generally evaluated to be the UCL and that the sound pressure monotonously descends in successive sound stimulations. For example, assuming that the HTL value at a given frequency is 50 dBHL, and the sound pressure of the first sound is 80 dBHL, then the sound pressure of the second sound may be determined as 75 dBHL, and the sound pressure of the third sound as 70 dBHL. Alternatively, the sound pressure of the first sound may be determined as 80 dBHL, the sound pressure of the second sound as 70 dBHL, and the sound pressure of the third sound as 60 dBHL. Together with the information received from the sound stimulation group determination section 70, the sound pressure of each sound stimulation in the sound stimulation group is sent to the sound stimulation generation section 75.

<Step S108>

The sound stimulation generation section 75 generates sound stimulation data based on the sound stimulation information received from the sound stimulation sound pressure determination section 71. Each sound stimulation may be a tone burst sound with a rise and fall of 3 ms, for example.

<Step S109>

With the timing of sound stimulation presentation received from the sound stimulation scheduling section 90, the sound stimulation generation section 75 outputs the sound stimulations to the user via the sound stimulation output section 10. Moreover, at this timing, the sound stimulation generation section 75 outputs a trigger signal to the biological signal measurement section 50. The sound stimulation generation section 75 may generate one piece of sound stimulation data for one sound stimulation group. A piece of sound stimulation data thus generated contains data corresponding to a plurality of sound stimulations which undergo changes in sound pressure at a predetermined time interval. In that case, the trigger signal to be sent to the biological signal measurement section 50 may only be sent at the timing of presenting the first sound.

<Step S110>

Based on the electroencephalogram and trigger information received from the biological signal measurement section 50, the event-related potential characteristic amount extraction section 55 cuts out an event-related potential in a predetermined zone which is defined based on the trigger information as a starting point (e.g., a zone from 100 ms before the presentation of the first sound to 400 ms after the presentation of the third sound).

At step S111, in accordance with the particulars of the sound stimulations received from the sound pressure determination section 71, the characteristic amount extraction section 55 calculates respective wavelet-coefficient related characteristic amounts for the first to third sounds.

<Step S112>

Based on the sound stimulation information received from the sound stimulation sound pressure determination section 71, the characteristic amount extraction section 55 takes an arithmetic mean of the wavelet coefficients calculated at step S107 for each of the right or left ear and each frequency.

<Step S113>

The characteristic amount extraction section 55 determines whether the number of summations (in the arithmetic mean) for the sound stimulations of the sound stimulation group presented at step S105 has reached a predetermined number of times. If the number of summations is less than the predetermined number of times, the process returns to step S103 to repeat presentation of the sound stimulation group. If the number of summations is equal to or greater than the predetermined number of times, the event-related potential characteristic amount extraction section 55 sends the arithmetic-meaned wavelet-coefficient related characteristic amount to the uncomfortable sound pressure determination section 65.

Thereafter, the process proceeds to step S109. The predetermined number of times may be 20 times, for example. Note that "20 times" is a mere example, although it is a number of summations which is frequently adopted in fields where event-related potentials are to be measured; it will be appreciated that any arbitrary number of times may be adopted.

<Step S114>

By using the respective wavelet-coefficient related characteristic amounts for the first to third sounds received from the event-related potential characteristic amount extraction section 55, the uncomfortable sound pressure determination section 65 determines an uncomfortable sound pressure of the user 5. The uncomfortable sound pressure determination can be achieved through a linear discrimination utilizing wavelet characteristic amounts of other people which are prepared in advance and training data for subjective UCL values. The training data which is utilized for uncomfortable sound pressure estimation may be switched so that the right or left ear and frequency of the training data match the right or left ear and frequency of the one who is the subject of determination. Moreover, the training data may be switched according to the user's symptoms of hypacusia. For example, training data may be prepared and switched between general categories, e.g., conductive deafness and perceptive deafness. Also, training data may be prepared and switched according to the audiogram pattern, e.g., gradual low tone loss or gradual high tone loss.

<Step S115>

For each of the right or left ear and for each frequency of the sound stimulation group presented at step S105, the result accumulating DB 80 accumulates the information of uncomfortable sound pressure determination results received from the uncomfortable sound pressure determination section 65.

With the uncomfortable sound pressure estimation system 100 of the present embodiment, three successive sounds of the same frequency that monotonously descend in sound pressures are timely presented so that periodic noises are not likely to affect the accuracy of estimation, and electroencephalographic characteristic amounts are respectively extracted for the sound stimulations of first to third sounds. Moreover, an uncomfortable sound pressure is estimated from the change pattern in the extracted characteristic amounts. This realizes a hearing aid fitting which does not allow the user to experience an uncomfortable sound pressure upon wearing a hearing aid, even if the user is wearing a pacemaker.

(Other Embodiments)

Embodiment 1 illustrates a case where the timing of presenting three successive sounds that monotonously descend in sound pressures is controlled so as not to be affected by periodic noises, and an uncomfortable sound pressure of the user is measured electroencephalogram analysis. However, this is only an exemplary embodiment. Based on the concept disclosed in the present specification of setting an analysis-pertinent zone so as to fall in a zone of low noise influence, various modifications would be possible for scheduling the stimulation timing in measuring any other component of event-related potential for any other purpose. For example, in the case of relying on the presence or absence of an N1 component of event-related potential in determining whether a sound stimulation was heard or not, a latency of 80 ms-150 ms, at which the N1 component will be induced, defines the analysis-pertinent zone. The timing of sound stimulation presentation may be set so that this analysis-pertinent zone does not fall into a zone of low noise influence.

In the description of Embodiment 1, it is illustrated that the biological signal measurement section 50 cuts out an event-related potential in a predetermined range based on trigger information from the sound stimulation generation section 75 as a starting point, and sends it to the event-related potential characteristic amount extraction section 55. However, this process is an example. In another process, for example, the biological signal measurement section 50 may constantly measure an electroencephalogram, and the characteristic amount extraction section 55 may perform cutting out of an event-related potential and a baseline correction as needed. With such a construction, the sound stimulation generation section 75 does not need to send trigger information to the biological signal measurement section 50, but may directly send a trigger signal to the characteristic amount extraction section 55.

Although Embodiment 1 illustrates that the results of uncomfortable sound pressure estimation are accumulated in the result accumulating DB 80, accumulation is not necessary. For example, in the case where the result accumulating DB 80 is provided external to the uncomfortable sound pressure estimation apparatus 1, each result of determination of the uncomfortable sound pressure determination section 65 may simply be output. Each result of determination can be utilized as information concerning uncomfortable sound pressure.

(Hearing Aid Adjustment)

The basic function of a hearing aid is sound amplification. The amount of amplification (gain) needs to be set for each user, according to individual differences in auditory characteristics. Therefore, prior to beginning use of a hearing aid, "fitting" is performed to set a gain of a hearing aid for each frequency. In order to realize appropriate fitting, it is essential to accurately measure the auditory characteristics of the user in the first place.

In an auditory characteristics test, a hearing threshold level (HTL) is first examined, and then an uncomfortable level (UCL) is examined. The HTL and UCL are used for determining a dynamic range of sound pressure in which to make an output from a hearing aid. The HTL, which is used for determining hypacusia, is a relatively simple test where an audiometer is employed to measure whether a sound was heard or not for each frequency. A diagram in which HTL is plotted for different frequencies (e.g. 250 Hz, 500 Hz, 1000 Hz, 2000 Hz, 4000 Hz) is called an audiogram. On the other hand, it is often the case that the UCL is calculated from the HTL for each frequency, because it would otherwise need to be measured while presenting uncomfortably loud sounds, which would induce psychological stress and fatigue. In the case where the UCL is to be measured through subjective reporting, continuous sounds or discontinuous sounds are presented to the user by ascending method (i.e., the sound pressure level is gradually increased) while using an audiometer, and the user is asked to report whether or not each sound pressure is so loud that it cannot be heard for a long time; the sound pressure of the user's own reporting is regarded as the UCL.

"Subjective reporting" means for a user, who hears a sound, to report on a subjective impression of that sound.

The gain of a hearing aid for each frequency and each sound pressure of input sound are to be determined by utilizing the aforementioned auditory characteristics and a mathematical function called a fitting theory. Currently, there exists no single fitting theory that is universally applicable to any and all users, and several fitting theories exist. For example, in the half-gain method, an insertion gain of each frequency is made half of the HTL for that frequency. Berger's method slightly augments the amplify from 1000 Hz to 4000 Hz by taking into consideration the frequency band and level of conversational voices. The POGO method, which is based on the half-gain method, reduces the gains at 250 Hz and 500 Hz (where there is not so much speech sound information but a lot of noise component is included) by 10 dB and 5 dB, respectively. The NAL-R method performs amplification so that a frequency of long-term sound analysis of words will fall around a comfortable level.

Examples of inappropriate fitting may be: (1) an insufficient amount of amplification for sound pressure; or (2) an excessive amount of amplification for sound pressure. For example, if the amount of amplification for sound pressure is insufficient, the user cannot aurally distinguish audios. In this case, the aforementioned purpose of using a hearing aid is not met. If the amount of amplification for sound pressure is excessive, the user is capable of aural distinction of audios, but may find the audio to be loud, which prevents the user from using the hearing aid over a long time. Therefore, a fitting of a hearing aid needs to be done in such a manner that neither (1) nor (2) occurs. Especially (2) possesses a possibility that the hearing aid may present an audio with an unduly high sound pressure to the user. This has created danger of hurting the user's ear with audios having high sound pressure.

In order to avoid problem (2), it is necessary that the UCL be correctly determined. However, a UCL which is calculated from the HTL does not reflect individual differences, and therefore contains an error due to an individual difference. Although a method of measuring a UCL through subjective reporting is also available, this can only provide a low precision because the criterion for UCL fluctuates from individual to individual, or under the influence of linguistic expressions.

In contrast, according to one embodiment of the uncomfortable sound pressure estimation system of the present disclosure as described above, an uncomfortable sound pressure of a user can be estimated with a good precision without presenting any overbearing sound stimulations, even if the user is wearing a device that generates periodic noises. Thus, appropriate fitting of a hearing aid can be achieved.

The uncomfortable sound pressure estimation system according to the present disclosure is useful for the adjustment of a hearing aid at a hearing aid shop or in households, etc.

While the present invention has been described with respect to exemplary embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An uncomfortable sound pressure estimation system comprising:
   one or more memories; and
   circuitry which in operation is configured to:
   measure an electroencephalogram signal of a user;
   present a sound stimulation group including a first sound, a second sound, and a third sound to the user, the first sound, the second sound, and the third sound having a same frequency and having sound pressures in a predetermined range;
   extract, from the electroencephalogram signal in a predetermined analysis zone defined based on a point of presenting at least one of the second sound and the third sound to the user as a starting point, a characteristic amount of event-related potential associated with at least one of the second sound and the third sound;

determine an uncomfortable sound pressure for the frequency of the sound stimulation group, based on the characteristic amount extracted;

extract, from the electroencephalogram signal of the user, a point of occurrence of at least one of a plurality of noises constituting periodic noises;

predict a next point of noise occurrence from the point of occurrence of the at least one noise extracted; and determine an output timing for the sound stimulation group so that an analysis zone for at least one of the second sound and third sound begins after a predetermined time has elapsed since the predicted next point of noise occurrence.

2. The uncomfortable sound pressure estimation system of claim 1, wherein the circuitry is configured to output the first sound, the second sound, and the third sound so as to consecutively decrease in sound pressure.

3. The uncomfortable sound pressure estimation system of claim 1, wherein the circuitry is configured to extract an N1-P2 amplitude or a wavelet-coefficient related characteristic amount.

4. The uncomfortable sound pressure estimation system of claim 1, wherein the circuitry is configured to subject the electroencephalogram signal of the user to differentiation, and if a result of the differentiation is equal to or greater than a predetermined threshold value, determines that noise has occurred.

5. The uncomfortable sound pressure estimation system of claim 1, wherein the circuitry is configured to calculate a period of periodic noise occurrences, and based on an average value or weighted average value of occurrence intervals between a past plurality of points of noise occurrence, predicts a next point of noise occurrence.

6. The uncomfortable sound pressure estimation system of claim 1, wherein the circuitry is configured to set an output timing for the sound stimulation group so that the analysis zone does not fall into a time slot which begins from 100 ms before the predicted next point of noise occurrence and spans 250 ms, the analysis zone being a zone from 0 ms to 300 ms after the third sound is output.

7. The uncomfortable sound pressure estimation system of claim 1, wherein the circuitry further is:

configured to determine the frequency of the sound stimulation group including the first sound, the second sound, and the third sound, each sound being a pure tone; and configured to determine the sound pressures of the first sound, the second sound, and the third sound so that the first sound, the second sound, and the third sound consecutively decrease in sound pressure in this order while being equal to or less than a predetermined threshold value, wherein the circuitry further is configured to output the first sound, the second sound, and the third sound at the determined frequency and at the determined sound pressures.

8. The uncomfortable sound pressure estimation system of claim 1, wherein, by referring to a time interval between the first sound and the second sound, the circuitry determines the points in time of outputting the first sound, the second sound, and the third sound so that times of measurement for event-related potentials in response to the second sound and third sound arrive after a predetermined noise-lingering time has elapsed since the predicted next point of noise occurrence.

9. The uncomfortable sound pressure estimation system of claim 1, wherein the determines the points in time of outputting the first sound, the second sound, and the third sound so that, if a time interval with which the periodic noises have occurred is shorter than a time from a point of beginning measurement of the event-related potential in response to the second sound till a point of ending measurement of the event-related potential in response to the third sound, the analysis zone for the third sound begins after a predetermined noise-lingering time has elapsed since the predicted next point of noise occurrence.

10. An uncomfortable sound pressure estimation apparatus comprising:

one or more memories; and circuitry which in operation is configured to:

receive a next point of noise occurrence predicted based on a time interval with which periodic noises occur, the time interval being obtained from an electroencephalogram signal of a user measured by a biological signal measurement device configured to measure an electroencephalogram signal of the user, and based on a previously-retained interval between a first sound, a second sound, and a third sound, determining points in time of outputting the first sound, the second sound, and the third sound so that times of measurement for event-related potentials in response to the second sound and third sound arrive after a predetermined noise-lingering time has elapsed since the predicted next point of noise occurrence;

receive the determined points in time of outputting the first sound, the second sound, and the third sound and, from the electroencephalogram signal of the user measured by the biological signal measurement device, extract a characteristic amount of an event-related potential of the electroencephalogram signal based on the point in time of outputting each of the first sound, the second sound, and the third sound as a starting point; and determine an uncomfortable sound pressure for a frequency of the sound stimulation group, based on the extracted characteristic amounts extracted by the characteristic amount extraction section.

11. An uncomfortable sound pressure estimation system, comprising:

one or more memories; and circuitry which in operation is configured to:

measure an electroencephalogram signal of a user;

present a sound stimulation to the user;

extract a characteristic amount of an event-related potential associated with the sound stimulation, from the electroencephalogram signal in a predetermined analysis zone defined based on a point in time of presenting the sound stimulation as a starting point;

determine an uncomfortable sound pressure for a frequency of the sound stimulation group, based on the extracted characteristic amount;

extract, from the electroencephalogram signal of the user, a point of occurrence of at least one of a plurality of noises constituting periodic noises;

predict a next point of noise occurrence from the point of occurrence of the at least one noise extracted; and determine an output timing for the sound stimulation, based on the predicted next point of noise occurrence.

12. An uncomfortable sound pressure estimation method, comprising:

a first biological signal measuring step of measuring an electroencephalogram signal of a user;

a noise extracting step of, from the electroencephalogram signal of the user measured by the first biological signal measuring step, extracting a point of occurrence of at least one of a plurality of noises constituting periodic noises;

a noise occurrence predicting step of predicting a next point of noise occurrence from the point of occurrence of the at least one noise extracted by the noise extracting step;

a sound stimulation scheduling step of, prior to presenting a sound stimulation group including a first sound, a second sound, and a third sound to the user, the first sound, the second sound, and the third sound having a same frequency and sound pressures in a predetermined range, determining an output timing for the sound stimulation group so that an analysis zone for at least one of the second sound and third sound begins after a predetermined time has elapsed since the predicted next point of noise occurrence;

an outputting step of, with the output timing determined by the sound stimulation scheduling step, presenting to the user the sound stimulation group including the first sound, the second sound, and the third sound having the same frequency and sound pressures in the predetermined range;

a second biological signal measuring step of measuring an electroencephalogram signal of the user when the sound stimulation group is presented with the output timing in the outputting step;

a characteristic amount extracting step of, from the electroencephalogram signal measured by the second biological signal measuring step in a predetermined analysis zone defined based on a point in time of presenting at least one of the second sound and the third sound to the user as a starting point, extracting a characteristic amount of an event-related potential associated with at least one of the second sound and the third sound; and an uncomfortable sound pressure determining step of determining an uncomfortable sound pressure for the frequency of the sound stimulation group, based on the characteristic amount extracted by the characteristic amount extracting step.

13. A non-transitory computer readable medium storing a computer program to be executed by a computer mounted in an uncomfortable sound pressure estimation apparatus of an uncomfortable sound pressure estimation system, wherein the computer program causes the computer to execute:

a first biological signal measuring step of acquiring an electroencephalogram signal of a user;

a noise extracting step of, from the electroencephalogram signal of the user acquired by the first biological signal measuring step, extracting a point of occurrence of at least one of a plurality of noises constituting periodic noises;

a noise occurrence predicting step of predicting a next point of noise occurrence from the point of occurrence of the at least one noise extracted by the noise extracting step;

a sound stimulation scheduling step of, prior to presenting a sound stimulation group including a first sound, a second sound, and a third sound to the user, the first sound, the second sound, and the third sound having a same frequency and sound pressures in a predetermined range, determining an output timing for the sound stimulation group so that an analysis zone for at least one of the second sound and third sound begins after a predetermined time has elapsed since the predicted next point of noise occurrence;

an outputting step of, with the output timing determined by the sound stimulation scheduling step, presenting to the user the sound stimulation group including the first sound, the second sound, and the third sound having the same frequency and sound pressures in the predetermined range;

a second biological signal measuring step of acquiring an electroencephalogram signal of the user when the sound stimulation group is presented with the output timing in the outputting step;

a characteristic amount extracting step of, from the electroencephalogram signal acquired by the second biological signal measuring step in a predetermined analysis zone defined based on a point in time of presenting at least one of the second sound and the third sound to the user as a starting point, extracting a characteristic amount of an event-related potential associated with at least one of the second sound and the third sound; and an uncomfortable sound pressure determining step of determining an uncomfortable sound pressure for the frequency of the sound stimulation group, based on the characteristic amount extracted by the characteristic amount extracting step.

* * * * *